(12) United States Patent
Sjolund et al.

(10) Patent No.: US 11,806,514 B2
(45) Date of Patent: Nov. 7, 2023

(54) MEDICINE INJECTION AND DISEASE MANAGEMENT SYSTEMS, DEVICES, AND METHODS

(71) Applicant: Bigfoot Biomedical, Inc., Milpitas, CA (US)

(72) Inventors: Per John Sjolund, Los Altos, CA (US); Lane Desborough, Thousand Oaks, CA (US); Bryan Mazlish, Palo Alto, CA (US); Andrew Bochenko, Redwood City, CA (US); Ross Naylor, Fullerton, CA (US)

(73) Assignee: Bigfoot Biomedical, Inc., Milpitas, CA (US)

( * ) Notice: Subject to any disclaimer, the term of this patent is extended or adjusted under 35 U.S.C. 154(b) by 0 days.

(21) Appl. No.: 16/566,544

(22) Filed: Sep. 10, 2019

(65) Prior Publication Data
US 2020/0001018 A1 Jan. 2, 2020

Related U.S. Application Data

(63) Continuation of application No. 15/717,805, filed on Sep. 27, 2017, now Pat. No. 10,426,896.
(Continued)

(51) Int. Cl.
*A61M 5/32* (2006.01)
*G06F 3/04817* (2022.01)
(Continued)

(52) U.S. Cl.
CPC ........ *A61M 5/3202* (2013.01); *A61M 5/1723* (2013.01); *G06F 3/0482* (2013.01);
(Continued)

(58) Field of Classification Search
CPC .............. A61M 5/3202; A61M 5/1723; A61M 2205/3303; A61M 2205/3306;
(Continued)

(56) References Cited

U.S. PATENT DOCUMENTS 2,605,765 A 8/1952 Kollsman
3,886,938 A 6/1975 Szabo et al.
(Continued)

FOREIGN PATENT DOCUMENTS

CA 2543545 A1 5/2005
CN 104620244 A 5/2015
(Continued)

OTHER PUBLICATIONS

Owens et al., Run-to-Run Control of Blood Glucose Concentrations for People with Type 1 Diabetes Mellitus, IEEE 2006, pp. 996-1005. (Year: 2006).*
(Continued)

*Primary Examiner* — Alvin H Tan
(74) *Attorney, Agent, or Firm* — TraskBritt

(57) ABSTRACT

One or more embodiments of the present disclosure may include an insulin delivery system that includes an insulin delivery device, a user interface that includes multiple user-selectable icons or buttons each representing different meal characteristics, memory to store one or more user-specific dosage parameter, and a processor in communication with the memory and adapted to receive blood glucose data. The processor may also be adapted to determine initial meal characteristics associated with each of the user-selectable icons or buttons based on at least one of the user-specific dosage parameters. The processor may also be adapted to update the meal characteristics associated with each of the user-selectable icons or buttons based upon the blood glucose data.

20 Claims, 14 Drawing Sheets

Related U.S. Application Data

(60) Provisional application No. 62/400,366, filed on Sep. 27, 2016.

(51) Int. Cl.

| | | |
|---|---|---|
| *G16H 20/17* | (2018.01) | |
| *G16H 50/20* | (2018.01) | |
| *G16H 20/10* | (2018.01) | |
| *A61M 5/172* | (2006.01) | |
| *G06F 3/0482* | (2013.01) | |
| *G06F 3/04847* | (2022.01) | |
| *G16H 10/60* | (2018.01) | |
| *G16H 40/63* | (2018.01) | |
| *G06F 3/04883* | (2022.01) | |

(52) U.S. Cl.
CPC ...... *G06F 3/04817* (2013.01); *G06F 3/04847* (2013.01); *G16H 20/10* (2018.01); *G16H 20/17* (2018.01); *G16H 50/20* (2018.01); *A61M 2205/3303* (2013.01); *A61M 2205/3306* (2013.01); *A61M 2205/3561* (2013.01); *A61M 2205/50* (2013.01); *A61M 2205/505* (2013.01); *A61M 2205/52* (2013.01); *A61M 2230/201* (2013.01); *G06F 3/04883* (2013.01); *G16H 10/60* (2018.01); *G16H 40/63* (2018.01)

(58) Field of Classification Search
CPC ...... A61M 2205/3561; A61M 2205/50; A61M 2205/505; A61M 2205/52; A61M 2230/201; G16H 20/17; G16H 50/20; G16H 20/10; G06F 3/04817; G06F 3/0482; G06F 3/04847; G06F 19/3468
USPC ........................................................ 715/771
See application file for complete search history.

(56) References Cited

U.S. PATENT DOCUMENTS

| | | |
|---|---|---|
| 4,077,405 A | 3/1978 | Haerten et al. |
| 4,231,368 A | 11/1980 | Becker |
| 4,265,241 A | 5/1981 | Portner et al. |
| 4,300,554 A | 11/1981 | Hessberg et al. |
| 4,313,439 A | 2/1982 | Babb et al. |
| 4,398,908 A | 8/1983 | Siposs |
| 4,435,173 A | 3/1984 | Siposs et al. |
| 4,443,218 A | 4/1984 | Decant et al. |
| 4,493,704 A | 1/1985 | Beard et al. |
| 4,529,401 A | 7/1985 | Leslie et al. |
| 4,681,569 A | 7/1987 | Coble et al. |
| 4,749,109 A | 6/1988 | Kamen |
| 4,838,857 A | 6/1989 | Strowe et al. |
| 4,850,817 A | 7/1989 | Nason et al. |
| 5,045,064 A | 9/1991 | Idriss |
| 5,088,981 A | 2/1992 | Howson et al. |
| 5,088,990 A | 2/1992 | Hivale et al. |
| D325,781 S | 4/1992 | Moller-Jensen |
| 5,190,522 A | 3/1993 | Wojcicki et al. |
| 5,225,763 A | 7/1993 | Krohn et al. |
| 5,250,027 A | 10/1993 | Lewis et al. |
| 5,261,882 A | 11/1993 | Sealfon |
| 5,314,412 A | 5/1994 | Rex |
| 5,335,994 A | 8/1994 | Weynant |
| 5,338,157 A | 8/1994 | Blomquist |
| 5,342,180 A | 8/1994 | Daoud |
| D351,469 S | 10/1994 | Okamoto |
| 5,389,078 A | 2/1995 | Zalesky et al. |
| 5,395,340 A | 3/1995 | Lee |
| 5,411,487 A | 5/1995 | Castagna |
| 5,545,143 A | 8/1996 | Fischell et al. |
| 5,551,850 A | 9/1996 | Williamson et al. |
| 5,554,123 A | 9/1996 | Herskowitz |
| 5,569,186 A | 10/1996 | Lord et al. |
| 5,626,566 A | 5/1997 | Petersen et al. |
| 5,637,095 A | 6/1997 | Nason et al. |
| 5,640,954 A | 6/1997 | Pfeiffer et al. |
| 5,665,065 A | 9/1997 | Colman et al. |
| 5,678,571 A | 10/1997 | Brown |
| 5,718,562 A | 2/1998 | Lawless et al. |
| D393,264 S | 4/1998 | Leung |
| 5,741,216 A | 4/1998 | Hemmingsen et al. |
| 5,766,155 A | 6/1998 | Hyman et al. |
| 5,772,635 A | 6/1998 | Dastur et al. |
| 5,816,306 A | 10/1998 | Giacomel |
| 5,852,803 A | 12/1998 | Ashby et al. |
| 5,858,001 A | 1/1999 | Tsals et al. |
| 5,918,603 A | 7/1999 | Brown |
| 5,919,167 A | 7/1999 | Mulhauser et al. |
| 5,925,018 A | 7/1999 | Ungerstedt |
| 5,928,201 A | 7/1999 | Poulsen et al. |
| 5,947,934 A | 9/1999 | Hansen et al. |
| 5,951,530 A | 9/1999 | Steengaard et al. |
| 5,957,889 A | 9/1999 | Poulsen et al. |
| 5,984,894 A | 11/1999 | Poulsen et al. |
| 5,984,897 A | 11/1999 | Petersen et al. |
| 5,997,475 A | 12/1999 | Bortz |
| 6,003,736 A | 12/1999 | Ljunggren |
| 6,010,485 A | 1/2000 | Buch-Rasmussen et al. |
| 6,032,119 A | 2/2000 | Brown et al. |
| 6,033,377 A | 3/2000 | Rasmussen et al. |
| 6,045,537 A | 4/2000 | Klitmose |
| D424,036 S | 5/2000 | Arora et al. |
| 6,056,728 A | 5/2000 | Von Schuckmann |
| 6,074,372 A | 6/2000 | Hansen |
| 6,110,149 A | 8/2000 | Klitgaard et al. |
| 6,156,014 A | 12/2000 | Petersen et al. |
| 6,171,276 B1 | 1/2001 | Lippe et al. |
| 6,231,540 B1 | 5/2001 | Smedegaard |
| 6,248,067 B1 | 6/2001 | Causey et al. |
| 6,248,090 B1 | 6/2001 | Jensen et al. |
| 6,248,093 B1 | 6/2001 | Moberg |
| 6,277,098 B1 | 8/2001 | Klitmose et al. |
| 6,302,855 B1 | 10/2001 | Lav et al. |
| 6,302,869 B1 | 10/2001 | Klitgaard |
| 6,354,996 B1 | 3/2002 | Drinan et al. |
| 6,368,314 B1 | 4/2002 | Kipfer et al. |
| 6,375,638 B2 | 4/2002 | Nason et al. |
| 6,379,339 B1 | 4/2002 | Klitgaard et al. |
| 6,381,496 B1 | 4/2002 | Meadows et al. |
| 6,404,098 B1 | 6/2002 | Kayama et al. |
| D460,053 S | 7/2002 | Choi |
| 6,427,088 B1 | 7/2002 | Bowman et al. |
| D461,241 S | 8/2002 | Moberg et al. |
| D461,891 S | 8/2002 | Moberg |
| 6,436,072 B1 | 8/2002 | Kullas et al. |
| 6,461,331 B1 | 10/2002 | Van Antwerp |
| 6,474,219 B2 | 11/2002 | Klitmose et al. |
| 6,485,461 B1 | 11/2002 | Mason et al. |
| 6,508,788 B2 | 1/2003 | Preuthun |
| 6,524,280 B2 | 2/2003 | Hansen et al. |
| 6,533,183 B2 | 3/2003 | Aasmul et al. |
| 6,537,251 B2 | 3/2003 | Klitmose |
| 6,540,672 B1 | 4/2003 | Simonsen et al. |
| 6,544,229 B1 | 4/2003 | Danby et al. |
| 6,547,764 B2 | 4/2003 | Larsen et al. |
| 6,551,276 B1 | 4/2003 | Mann et al. |
| 6,554,798 B1 | 4/2003 | Mann et al. |
| 6,554,800 B1 | 4/2003 | Nezhadian et al. |
| 6,558,320 B1 | 5/2003 | Causey et al. |
| 6,558,351 B1 | 5/2003 | Steil et al. |
| 6,562,001 B2 | 5/2003 | Lebel et al. |
| 6,562,011 B1 | 5/2003 | Buch-Rasmussen et al. |
| 6,564,105 B2 | 5/2003 | Starkweather et al. |
| 6,569,126 B1 | 5/2003 | Poulsen et al. |
| 6,571,128 B2 | 5/2003 | Lebel et al. |
| 6,577,899 B2 | 6/2003 | Lebel et al. |
| 6,582,404 B1 | 6/2003 | Klitgaard et al. |
| 6,585,644 B2 | 7/2003 | Lebel et al. |
| 6,585,699 B2 | 7/2003 | Ljunggreen et al. |
| 6,589,229 B1 | 7/2003 | Connelly et al. |
| 6,605,067 B1 | 8/2003 | Larsen |
| 6,613,019 B2 | 9/2003 | Munk |

(56) References Cited

U.S. PATENT DOCUMENTS

| | | |
|---|---|---|
| 6,641,533 B2 | 11/2003 | Causey et al. |
| 6,648,821 B2 | 11/2003 | Lebel et al. |
| 6,650,951 B1 | 11/2003 | Jones et al. |
| 6,656,158 B2 | 12/2003 | Mahoney et al. |
| 6,656,159 B2 | 12/2003 | Flaherty |
| 6,659,948 B2 | 12/2003 | Lebel et al. |
| 6,659,978 B1 | 12/2003 | Kasuga et al. |
| 6,659,980 B2 | 12/2003 | Moberg et al. |
| 6,663,602 B2 | 12/2003 | Schmidt |
| 6,668,196 B1 | 12/2003 | Villegas et al. |
| 6,669,669 B2 | 12/2003 | Flaherty et al. |
| 6,687,546 B2 | 2/2004 | Lebel et al. |
| 6,690,192 B1 | 2/2004 | Wing |
| 6,691,043 B2 | 2/2004 | Ribeiro, Jr. |
| 6,692,457 B2 | 2/2004 | Flaherty |
| 6,692,472 B2 | 2/2004 | Hansen et al. |
| 6,694,191 B2 | 2/2004 | Starkweather et al. |
| 6,699,218 B2 | 3/2004 | Flaherty et al. |
| 6,702,779 B2 | 3/2004 | Connelly et al. |
| 6,715,516 B2 | 4/2004 | Ohms et al. |
| 6,716,198 B2 | 4/2004 | Larsen |
| 6,723,072 B2 | 4/2004 | Flaherty et al. |
| 6,733,446 B2 | 5/2004 | Lebel et al. |
| 6,736,796 B2 | 5/2004 | Shekalim |
| 6,740,059 B2 | 5/2004 | Flaherty |
| 6,740,072 B2 | 5/2004 | Starkweather et al. |
| 6,740,075 B2 | 5/2004 | Lebel et al. |
| 6,744,350 B2 | 6/2004 | Blomquist |
| 6,749,587 B2 | 6/2004 | Flaherty |
| 6,752,787 B1 | 6/2004 | Causey et al. |
| 6,758,810 B2 | 7/2004 | Lebel et al. |
| 6,768,425 B2 | 7/2004 | Flaherty et al. |
| 6,780,156 B2 | 8/2004 | Haueter et al. |
| 6,786,246 B2 | 9/2004 | Ohms et al. |
| 6,786,890 B2 | 9/2004 | Preuthun et al. |
| 6,796,970 B1 | 9/2004 | Klitmose et al. |
| 6,799,149 B2 | 9/2004 | Hartlaub |
| 6,809,653 B1 | 10/2004 | Mann et al. |
| 6,810,290 B2 | 10/2004 | Lebel et al. |
| 6,811,533 B2 | 11/2004 | Lebel et al. |
| 6,811,534 B2 | 11/2004 | Bowman et al. |
| 6,813,519 B2 | 11/2004 | Lebel et al. |
| 6,827,702 B2 | 12/2004 | Lebel et al. |
| 6,830,558 B2 | 12/2004 | Flaherty et al. |
| 6,852,104 B2 | 2/2005 | Blomquist |
| 6,854,620 B2 | 2/2005 | Ramey |
| 6,854,653 B2 | 2/2005 | Eilersen |
| 6,855,129 B2 | 2/2005 | Jensen et al. |
| 6,872,200 B2 | 3/2005 | Mann et al. |
| 6,873,268 B2 | 3/2005 | Lebel et al. |
| 6,878,132 B2 | 4/2005 | Kipfer |
| 6,893,415 B2 | 5/2005 | Madsen et al. |
| 6,899,695 B2 | 5/2005 | Herrera |
| 6,899,699 B2 | 5/2005 | Enggaard |
| 6,922,590 B1 | 7/2005 | Whitehurst |
| 6,936,006 B2 | 8/2005 | Sabra |
| 6,936,029 B2 | 8/2005 | Mann et al. |
| 6,945,961 B2 | 9/2005 | Miller et al. |
| 6,948,918 B2 | 9/2005 | Hansen |
| 6,950,708 B2 | 9/2005 | Bowman et al. |
| 6,956,572 B2 | 10/2005 | Zaleski |
| 6,960,192 B1 | 11/2005 | Flaherty et al. |
| 6,979,326 B2 | 12/2005 | Mann et al. |
| 6,997,911 B2 | 2/2006 | Klitmose |
| 6,997,920 B2 | 2/2006 | Mann et al. |
| 7,005,078 B2 | 2/2006 | Van et al. |
| 7,008,399 B2 | 3/2006 | Larsen et al. |
| 7,014,625 B2 | 3/2006 | Bengtsson |
| 7,018,360 B2 | 3/2006 | Flaherty et al. |
| 7,025,743 B2 | 4/2006 | Mann et al. |
| 7,029,455 B2 | 4/2006 | Flaherty |
| 7,054,836 B2 | 5/2006 | Christensen et al. |
| 7,096,431 B2 | 8/2006 | Tambata et al. |
| 7,104,972 B2 | 9/2006 | Moller et al. |
| 7,109,878 B2 | 9/2006 | Mann et al. |
| 7,128,727 B2 | 10/2006 | Flaherty et al. |
| 7,133,329 B2 | 11/2006 | Skyggebjerg et al. |
| 7,232,423 B2 | 6/2007 | Mernoee |
| D545,837 S | 7/2007 | Haldimann et al. |
| 7,241,265 B2 | 7/2007 | Cummings et al. |
| D550,227 S | 9/2007 | Sato et al. |
| D553,625 S | 10/2007 | Burns et al. |
| D554,140 S | 10/2007 | Armendariz |
| 7,291,107 B2 | 11/2007 | Hellwig et al. |
| 7,343,197 B2 | 3/2008 | Shusterman |
| 7,454,359 B2 | 11/2008 | Rosenfeld et al. |
| 7,479,949 B2 | 1/2009 | Jobs et al. |
| D592,223 S | 5/2009 | Neuhaus |
| 7,534,226 B2 | 5/2009 | Mernoe et al. |
| 7,553,281 B2 | 6/2009 | Hellwig et al. |
| 7,555,727 B2 | 6/2009 | Hawkins et al. |
| 7,570,980 B2 | 8/2009 | Ginsberg |
| D600,341 S | 9/2009 | Loerwald |
| D603,421 S | 11/2009 | Ebeling et al. |
| D607,099 S | 12/2009 | Loerwald |
| 7,647,237 B2 | 1/2010 | Malave et al. |
| D614,587 S | 4/2010 | Yodfat et al. |
| 7,695,434 B2 | 4/2010 | Malecha |
| 7,708,717 B2 | 5/2010 | Estes et al. |
| 7,717,903 B2 | 5/2010 | Estes et al. |
| 7,751,907 B2 | 7/2010 | Blomquist |
| D623,753 S | 9/2010 | Saffer et al. |
| 7,789,859 B2 | 9/2010 | Estes et al. |
| D628,107 S | 11/2010 | Lee |
| 7,828,528 B2 | 11/2010 | Estes et al. |
| 7,837,647 B2 | 11/2010 | Estes et al. |
| 7,850,641 B2 | 12/2010 | Lebel et al. |
| 7,871,376 B2 | 1/2011 | Brown |
| D632,699 S | 2/2011 | Judy et al. |
| 7,878,975 B2 | 2/2011 | Liljeryd et al. |
| 7,887,512 B2 | 2/2011 | Estes et al. |
| 7,931,613 B2 | 4/2011 | Haueter et al. |
| 7,938,797 B2 | 5/2011 | Estes |
| D640,269 S | 6/2011 | Chen |
| 7,956,845 B2 | 6/2011 | Lee |
| D642,191 S | 7/2011 | Barnett et al. |
| D644,242 S | 8/2011 | Matas |
| D644,243 S | 8/2011 | Matas |
| 8,012,119 B2 | 9/2011 | Estes et al. |
| D648,804 S | 11/2011 | Coulter |
| D652,426 S | 1/2012 | Anzures |
| 8,132,101 B2 | 3/2012 | Buck et al. |
| D656,950 S | 4/2012 | Shallcross et al. |
| 8,156,070 B2 | 4/2012 | Buck et al. |
| D660,315 S | 5/2012 | Anzures |
| D661,701 S | 6/2012 | Brown et al. |
| 8,202,249 B2 | 6/2012 | Iio et al. |
| 8,217,946 B2 | 7/2012 | Halpern et al. |
| 8,219,222 B2 | 7/2012 | Blomquist |
| 8,221,345 B2 | 7/2012 | Blomquist |
| 8,221,359 B2 | 7/2012 | Kristensen et al. |
| 8,231,562 B2 | 7/2012 | Buck et al. |
| D665,409 S | 8/2012 | Gupta et al. |
| 8,237,715 B2 | 8/2012 | Buck et al. |
| 8,250,483 B2 | 8/2012 | Blomquist |
| 8,257,652 B2 | 9/2012 | Drucker et al. |
| 8,257,653 B2 | 9/2012 | Drucker et al. |
| 8,262,616 B2 | 9/2012 | Grant et al. |
| 8,273,296 B2 | 9/2012 | Drucker et al. |
| D669,165 S | 10/2012 | Estes et al. |
| D669,166 S | 10/2012 | Estes et al. |
| D669,167 S | 10/2012 | Estes et al. |
| 8,279,226 B2 | 10/2012 | Krieftewirth |
| 8,310,415 B2 | 11/2012 | Mclaughlin et al. |
| 8,337,469 B2 | 12/2012 | Eberhart et al. |
| D674,405 S | 1/2013 | Guastella et al. |
| 8,357,091 B2 | 1/2013 | Say et al. |
| 8,365,065 B2 | 1/2013 | Gejdos et al. |
| 8,372,005 B2 | 2/2013 | Say et al. |
| D682,289 S | 5/2013 | Dijulio et al. |
| D682,304 S | 5/2013 | Mierau et al. |
| D682,305 S | 5/2013 | Mierau et al. |
| 8,439,834 B2 | 5/2013 | Schmelzeisen-Redeker et al. |
| D683,738 S | 6/2013 | Wujcik et al. |

(56) References Cited

U.S. PATENT DOCUMENTS

| | | |
|---|---|---|
| D687,062 S | 7/2013 | Gardner et al. |
| D687,541 S | 8/2013 | Estes et al. |
| 8,514,086 B2 | 8/2013 | Harper et al. |
| D689,087 S | 9/2013 | Fymat |
| D689,090 S | 9/2013 | Impas et al. |
| D689,523 S | 9/2013 | Galbraith et al. |
| D689,874 S | 9/2013 | Brinda et al. |
| 8,529,838 B2 | 9/2013 | Drucker et al. |
| 8,529,839 B2 | 9/2013 | Drucker et al. |
| 8,529,841 B2 | 9/2013 | Drucker et al. |
| D690,717 S | 10/2013 | Thomsen et al. |
| D690,718 S | 10/2013 | Thomsen et al. |
| D691,258 S | 10/2013 | Estes et al. |
| D691,259 S | 10/2013 | Estes et al. |
| D693,114 S | 11/2013 | Lemanski, Sr. |
| D693,365 S | 11/2013 | Gardner et al. |
| D694,262 S | 11/2013 | Jang et al. |
| 8,579,815 B2 | 11/2013 | Galley et al. |
| 8,601,005 B2 | 12/2013 | Bousamra et al. |
| 8,615,366 B2 | 12/2013 | Galley et al. |
| D697,204 S | 1/2014 | Maier et al. |
| D697,519 S | 1/2014 | Thomsen et al. |
| 8,622,906 B2 | 1/2014 | Say et al. |
| D698,808 S | 2/2014 | Funabashi et al. |
| D699,741 S | 2/2014 | Wantland et al. |
| 8,657,779 B2 | 2/2014 | Blomquist |
| D701,879 S | 4/2014 | Foit et al. |
| D702,258 S | 4/2014 | Wantland et al. |
| D705,261 S | 5/2014 | Holz et al. |
| 8,719,945 B2 | 5/2014 | Birtwhistle et al. |
| 8,756,074 B2 | 6/2014 | Brzustowicz |
| 8,761,940 B2 | 6/2014 | Long et al. |
| D709,080 S | 7/2014 | Kim |
| D709,183 S | 7/2014 | Kemlein |
| D709,917 S | 7/2014 | Faulkner et al. |
| 8,774,887 B2 | 7/2014 | Say et al. |
| 8,816,862 B2 | 8/2014 | Harper et al. |
| 8,839,106 B2 | 9/2014 | Lee et al. |
| D714,816 S | 10/2014 | Varon |
| D715,835 S | 10/2014 | Montgomery et al. |
| D716,340 S | 10/2014 | Bresin et al. |
| D717,822 S | 11/2014 | Brotman et al. |
| D717,823 S | 11/2014 | Brotman et al. |
| D717,830 S | 11/2014 | Brinda et al. |
| D718,438 S | 11/2014 | Davis et al. |
| 8,895,315 B2 | 11/2014 | Batman et al. |
| D719,186 S | 12/2014 | Kim |
| 8,929,823 B2 | 1/2015 | Mears et al. |
| 8,961,465 B2 | 2/2015 | Blomquist |
| D724,616 S | 3/2015 | Jou |
| 8,992,464 B2 | 3/2015 | Bashan et al. |
| D727,336 S | 4/2015 | Allison et al. |
| 9,008,803 B2 | 4/2015 | Blomquist |
| 9,022,996 B2 | 5/2015 | Eberhart et al. |
| 9,033,877 B2 | 5/2015 | Werner et al. |
| 9,041,730 B2 | 5/2015 | Johnson et al. |
| D730,929 S | 6/2015 | Yu et al. |
| D731,525 S | 6/2015 | Myers |
| D733,175 S | 6/2015 | Bae |
| D733,179 S | 6/2015 | Kwon |
| 9,050,409 B2 | 6/2015 | Haueter et al. |
| 9,056,165 B2 | 6/2015 | Steil et al. |
| 9,072,477 B2 | 7/2015 | Say et al. |
| 9,076,107 B2 | 7/2015 | Cameron et al. |
| D736,792 S | 8/2015 | Brinda et al. |
| D737,278 S | 8/2015 | Shin et al. |
| D738,907 S | 9/2015 | Cabrera-Cordon et al. |
| D738,913 S | 9/2015 | Cabrera-Cordon et al. |
| D738,914 S | 9/2015 | Torres et al. |
| D739,878 S | 9/2015 | Baxley |
| 9,134,823 B2 | 9/2015 | Grant et al. |
| 9,136,939 B2 | 9/2015 | Galley et al. |
| 9,144,204 B2 | 9/2015 | Redmond et al. |
| D741,891 S | 10/2015 | Gardner et al. |
| 9,159,148 B2 | 10/2015 | Boyer et al. |
| 9,171,343 B1 * | 10/2015 | Fischell ............... A61M 5/1723 |
| D743,435 S | 11/2015 | Herold et al. |
| 9,186,113 B2 | 11/2015 | Harper et al. |
| D744,505 S | 12/2015 | Wilberding et al. |
| D745,050 S | 12/2015 | Kwon |
| D745,543 S | 12/2015 | Kim et al. |
| D746,314 S | 12/2015 | Jung et al. |
| 9,198,623 B2 | 12/2015 | Fern et al. |
| D746,848 S | 1/2016 | Bovet et al. |
| D748,646 S | 2/2016 | Kim et al. |
| D749,097 S | 2/2016 | Zou et al. |
| D750,663 S | 3/2016 | Mariet et al. |
| D751,081 S | 3/2016 | Kim et al. |
| D751,090 S | 3/2016 | Hu et al. |
| D751,585 S | 3/2016 | Kaufthal et al. |
| D751,586 S | 3/2016 | Kaufthal et al. |
| D752,604 S | 3/2016 | Zhang |
| D752,736 S | 3/2016 | Chandrasenan et al. |
| D753,139 S | 4/2016 | Bovet |
| D753,177 S | 4/2016 | Mierau et al. |
| D753,685 S | 4/2016 | Zimmerman et al. |
| D754,150 S | 4/2016 | Oh et al. |
| D754,670 S | 4/2016 | Park |
| D754,685 S | 4/2016 | Carlton et al. |
| D754,689 S | 4/2016 | Lee |
| D754,713 S | 4/2016 | Zhang et al. |
| D754,714 S | 4/2016 | Zhang et al. |
| D755,206 S | 5/2016 | Lee et al. |
| D755,830 S | 5/2016 | Chaudhri et al. |
| D757,026 S | 5/2016 | Lim et al. |
| D757,047 S | 5/2016 | Cornwell et al. |
| D758,433 S | 6/2016 | Lee et al. |
| D760,752 S | 7/2016 | Anzures et al. |
| D761,843 S | 7/2016 | Kim |
| D762,234 S | 7/2016 | Li et al. |
| D762,675 S | 8/2016 | Lim et al. |
| D763,285 S | 8/2016 | Chan et al. |
| D763,860 S | 8/2016 | Sunshine et al. |
| D763,921 S | 8/2016 | Dharwada et al. |
| D765,092 S | 8/2016 | Chaudhri et al. |
| D765,710 S | 9/2016 | Anzures et al. |
| D766,257 S | 9/2016 | Zhang et al. |
| D766,424 S | 9/2016 | Anderson et al. |
| D768,144 S | 10/2016 | Kim et al. |
| D768,687 S | 10/2016 | Bae et al. |
| D769,314 S | 10/2016 | Piroddi et al. |
| D769,322 S | 10/2016 | Rajeswaran et al. |
| D769,325 S | 10/2016 | Casalegno et al. |
| D771,672 S | 11/2016 | Tanabe et al. |
| D772,241 S | 11/2016 | Capano |
| D772,924 S | 11/2016 | Begin et al. |
| D773,510 S | 12/2016 | Foss et al. |
| D776,137 S | 1/2017 | Chaudhri et al. |
| D776,253 S | 1/2017 | Li |
| D776,702 S | 1/2017 | Huang et al. |
| D777,200 S | 1/2017 | Luo et al. |
| D777,204 S | 1/2017 | Lee et al. |
| D777,735 S | 1/2017 | Kim et al. |
| D777,906 S | 1/2017 | Anderson et al. |
| D781,305 S | 3/2017 | Lau |
| D781,908 S | 3/2017 | Bhandari et al. |
| D783,652 S | 4/2017 | Guan et al. |
| D784,372 S | 4/2017 | Kovchiy |
| D786,266 S | 5/2017 | Van et al. |
| D786,270 S | 5/2017 | Barry et al. |
| D788,138 S | 5/2017 | Lee et al. |
| D788,140 S | 5/2017 | Hemsley et al. |
| D788,145 S | 5/2017 | Sullivan et al. |
| D788,808 S | 6/2017 | Chaudhri et al. |
| D789,419 S | 6/2017 | Chaudhri et al. |
| D790,562 S | 6/2017 | Nageli et al. |
| D790,583 S | 6/2017 | Kay et al. |
| D791,806 S | 7/2017 | Brewington et al. |
| 9,707,336 B2 | 7/2017 | Dang et al. |
| D794,649 S | 8/2017 | Niijima et al. |
| D795,284 S | 8/2017 | Miller et al. |
| D795,294 S | 8/2017 | Faulkner et al. |
| 9,717,849 B2 | 8/2017 | Mhatre et al. |
| D797,123 S | 9/2017 | Lee et al. |

(56) References Cited

U.S. PATENT DOCUMENTS

| | | |
|---|---|---|
| D797,771 S | 9/2017 | Caporal et al. |
| D797,772 S | 9/2017 | Mizono et al. |
| D797,788 S | 9/2017 | Havranek, Jr. |
| D798,318 S | 9/2017 | Ferguson et al. |
| D798,895 S | 10/2017 | Kim et al. |
| D799,536 S | 10/2017 | Eder |
| D800,757 S | 10/2017 | Mullen et al. |
| D801,519 S | 10/2017 | Sabin et al. |
| D801,990 S | 11/2017 | Reissner et al. |
| D802,607 S | 11/2017 | Apodaca et al. |
| D803,850 S | 11/2017 | Chang et al. |
| D804,505 S | 12/2017 | Hoffman et al. |
| D804,516 S | 12/2017 | Dye et al. |
| D805,541 S | 12/2017 | Juliano |
| D806,117 S | 12/2017 | Springer |
| D806,748 S | 1/2018 | Van et al. |
| D806,749 S | 1/2018 | Van et al. |
| D806,750 S | 1/2018 | Van et al. |
| D808,417 S | 1/2018 | Mander et al. |
| D808,974 S | 1/2018 | Chiappone et al. |
| D809,134 S | 1/2018 | Crothall |
| 9,878,097 B2 | 1/2018 | Estes |
| D809,535 S | 2/2018 | Park et al. |
| D810,095 S | 2/2018 | Vali et al. |
| D812,072 S | 3/2018 | Hoffman |
| D815,665 S | 4/2018 | Li et al. |
| D816,093 S | 4/2018 | Mazur et al. |
| 9,931,454 B2 | 4/2018 | Lo et al. |
| D816,708 S | 5/2018 | Riedel et al. |
| D816,709 S | 5/2018 | Riedel et al. |
| D816,713 S | 5/2018 | Kang |
| D819,065 S | 5/2018 | Xie et al. |
| D819,067 S | 5/2018 | Behzadi et al. |
| D819,646 S | 6/2018 | Jow et al. |
| D820,304 S | 6/2018 | Coffman et al. |
| D821,437 S | 6/2018 | Chaudhri et al. |
| D822,708 S | 7/2018 | Ghosh |
| D823,859 S | 7/2018 | Boyd |
| D826,969 S | 8/2018 | Goyette et al. |
| D828,375 S | 9/2018 | Mok et al. |
| D828,377 S | 9/2018 | Dhide |
| D830,385 S | 10/2018 | Lepine et al. |
| D835,658 S | 12/2018 | Chan et al. |
| D835,659 S | 12/2018 | Anzures et al. |
| D837,809 S | 1/2019 | Kagatsume et al. |
| D839,287 S | 1/2019 | Hersh et al. |
| D839,294 S | 1/2019 | Mazlish et al. |
| 10,263,802 B2 | 4/2019 | Burns et al. |
| D852,816 S | 7/2019 | Baekelandt et al. |
| D852,817 S | 7/2019 | Aoshima |
| D852,837 S | 7/2019 | Mazlish et al. |
| D853,441 S | 7/2019 | Khandelwal |
| D857,724 S | 8/2019 | Clediere et al. |
| D858,566 S | 9/2019 | Bacchus |
| D858,567 S | 9/2019 | Bacchus |
| 10,410,538 B2 * | 9/2019 | Simpson .............. A61B 5/742 |
| D863,343 S | 10/2019 | Mazlish et al. |
| D864,239 S | 10/2019 | Hisada et al. |
| 10,426,896 B2 | 10/2019 | Desborough et al. |
| D865,813 S | 11/2019 | Lee et al. |
| D866,584 S | 11/2019 | Burroughs et al. |
| D867,601 S | 11/2019 | Henry et al. |
| D870,767 S | 12/2019 | Villafane |
| D875,111 S | 2/2020 | Clediere |
| D875,124 S | 2/2020 | Yan |
| 10,572,107 B1 | 2/2020 | Beebe et al. |
| D879,118 S | 3/2020 | Chen et al. |
| D880,497 S | 4/2020 | Boyd |
| D883,319 S | 5/2020 | Caro et al. |
| D884,007 S | 5/2020 | Uppala et al. |
| D884,716 S | 5/2020 | Tan et al. |
| D886,850 S | 6/2020 | Kim et al. |
| D888,748 S | 6/2020 | Valladares et al. |
| D890,206 S | 7/2020 | Felkins et al. |
| D910,063 S | 2/2021 | Brooks |
| D910,654 S | 2/2021 | Eder |
| D910,669 S | 2/2021 | Wuqiang |
| D920,349 S | 5/2021 | Clements et al. |
| D927,527 S | 8/2021 | Bragdon et al. |
| D931,898 S | 9/2021 | Demar |
| D937,312 S | 11/2021 | Ding et al. |
| D939,570 S | 12/2021 | Dye et al. |
| D940,156 S | 1/2022 | Butcher et al. |
| D944,772 S | 3/2022 | Kim |
| D944,824 S | 3/2022 | Wang et al. |
| 2001/0041869 A1 | 11/2001 | Causey et al. |
| 2001/0056262 A1 | 12/2001 | Cabiri et al. |
| 2002/0004651 A1 | 1/2002 | Ljunggreen et al. |
| 2002/0007154 A1 | 1/2002 | Hansen et al. |
| 2002/0040208 A1 | 4/2002 | Flaherty et al. |
| 2002/0091358 A1 | 7/2002 | Klitmose |
| 2002/0126036 A1 | 9/2002 | Flaherty et al. |
| 2002/0175931 A1 | 11/2002 | Holtz et al. |
| 2002/0177810 A1 | 11/2002 | Reilly et al. |
| 2003/0028089 A1 * | 2/2003 | Galley ............... A61B 5/14532 600/365 |
| 2003/0055380 A1 | 3/2003 | Flaherty |
| 2003/0065308 A1 | 4/2003 | Lebel et al. |
| 2003/0088238 A1 | 5/2003 | Poulsen et al. |
| 2003/0167035 A1 | 9/2003 | Flaherty et al. |
| 2003/0198558 A1 | 10/2003 | Nason et al. |
| 2003/0199825 A1 | 10/2003 | Flaherty |
| 2003/0216683 A1 | 11/2003 | Shekalim |
| 2004/0010207 A1 | 1/2004 | Flaherty et al. |
| 2004/0019325 A1 | 1/2004 | Shekalim |
| 2004/0064088 A1 | 4/2004 | Gorman et al. |
| 2004/0064096 A1 | 4/2004 | Flaherty et al. |
| 2004/0078028 A1 | 4/2004 | Flaherty et al. |
| 2004/0087894 A1 | 5/2004 | Flaherty |
| 2004/0092865 A1 | 5/2004 | Flaherty et al. |
| 2004/0092878 A1 | 5/2004 | Flaherty |
| 2004/0093331 A1 | 5/2004 | Garner et al. |
| 2004/0116866 A1 | 6/2004 | Gorman et al. |
| 2004/0127844 A1 | 7/2004 | Flaherty |
| 2004/0153032 A1 | 8/2004 | Garribotto et al. |
| 2004/0153257 A1 | 8/2004 | Munk |
| 2004/0171983 A1 | 9/2004 | Sparks et al. |
| 2004/0176727 A1 | 9/2004 | Shekalim |
| 2004/0204673 A1 | 10/2004 | Flaherty |
| 2004/0220551 A1 | 11/2004 | Flaherty et al. |
| 2004/0235446 A1 | 11/2004 | Flaherty et al. |
| 2004/0260233 A1 | 12/2004 | Garibotto et al. |
| 2005/0021005 A1 | 1/2005 | Flaherty et al. |
| 2005/0022274 A1 | 1/2005 | Campbell et al. |
| 2005/0038674 A1 | 2/2005 | Braig et al. |
| 2005/0044500 A1 | 2/2005 | Orimoto et al. |
| 2005/0065760 A1 | 3/2005 | Murtfeldt et al. |
| 2005/0090808 A1 | 4/2005 | Malave et al. |
| 2005/0090851 A1 | 4/2005 | Devlin |
| 2005/0095063 A1 | 5/2005 | Fathallah et al. |
| 2005/0114374 A1 | 5/2005 | Juszkiewicz et al. |
| 2005/0160858 A1 | 7/2005 | Mernoe |
| 2005/0171512 A1 | 8/2005 | Flaherty |
| 2005/0182366 A1 | 8/2005 | Vogt et al. |
| 2005/0192494 A1 | 9/2005 | Ginsberg |
| 2005/0192561 A1 | 9/2005 | Mernoe |
| 2005/0203461 A1 | 9/2005 | Flaherty et al. |
| 2005/0215982 A1 | 9/2005 | Malave et al. |
| 2005/0222645 A1 | 10/2005 | Malave et al. |
| 2005/0234404 A1 | 10/2005 | Vilks et al. |
| 2005/0238507 A1 | 10/2005 | Diianni et al. |
| 2005/0245878 A1 | 11/2005 | Mernoe et al. |
| 2005/0251097 A1 | 11/2005 | Mernoe |
| 2005/0267402 A1 | 12/2005 | Stewart et al. |
| 2005/0273059 A1 | 12/2005 | Mernoe et al. |
| 2006/0041229 A1 | 2/2006 | Garibotto et al. |
| 2006/0069382 A1 | 3/2006 | Pedersen |
| 2006/0074381 A1 | 4/2006 | Malave et al. |
| 2006/0095014 A1 | 5/2006 | Ethelfeld |
| 2006/0135913 A1 | 6/2006 | Ethelfeld |
| 2006/0142698 A1 | 6/2006 | Ethelfeld |
| 2006/0151545 A1 | 7/2006 | Imhof et al. |
| 2006/0178633 A1 | 8/2006 | Garibotto et al. |
| 2006/0184119 A1 | 8/2006 | Remde et al. |

(56) References Cited

U.S. PATENT DOCUMENTS

| | | |
|---|---|---|
| 2006/0200073 A1 | 9/2006 | Radmer et al. |
| 2006/0206054 A1 | 9/2006 | Shekalim |
| 2006/0247581 A1 | 11/2006 | Pedersen et al. |
| 2006/0276771 A1 | 12/2006 | Galley et al. |
| 2007/0073228 A1 | 3/2007 | Mernoe et al. |
| 2007/0073235 A1 | 3/2007 | Estes et al. |
| 2007/0073236 A1 | 3/2007 | Mernoe et al. |
| 2007/0088271 A1 | 4/2007 | Richards |
| 2007/0106218 A1 | 5/2007 | Yodfat et al. |
| 2007/0124002 A1 | 5/2007 | Estes et al. |
| 2007/0156092 A1 | 7/2007 | Estes et al. |
| 2007/0167905 A1 | 7/2007 | Estes et al. |
| 2007/0167912 A1 | 7/2007 | Causey et al. |
| 2007/0171087 A1 | 7/2007 | Shimazu et al. |
| 2007/0179444 A1 | 8/2007 | Causey et al. |
| 2007/0213657 A1 | 9/2007 | Jennewine et al. |
| 2007/0239116 A1 | 10/2007 | Follman et al. |
| 2008/0051716 A1 | 2/2008 | Stutz |
| 2008/0059158 A1 | 3/2008 | Matsuo et al. |
| 2008/0097381 A1 | 4/2008 | Moberg et al. |
| 2008/0119705 A1 | 5/2008 | Patel et al. |
| 2008/0172026 A1 | 7/2008 | Blomquist |
| 2008/0201325 A1 | 8/2008 | Doniger et al. |
| 2008/0208627 A1 | 8/2008 | Skyggebjerg |
| 2008/0220752 A1 | 9/2008 | Forstall et al. |
| 2008/0262469 A1 | 10/2008 | Brister et al. |
| 2008/0287755 A1 | 11/2008 | Sass et al. |
| 2008/0287922 A1 | 11/2008 | Panduro |
| 2008/0294094 A1 | 11/2008 | Mhatre et al. |
| 2008/0294108 A1 | 11/2008 | Briones et al. |
| 2008/0294109 A1 | 11/2008 | Estes et al. |
| 2008/0294142 A1 | 11/2008 | Patel et al. |
| 2008/0300534 A1 | 12/2008 | Blomquist |
| 2008/0306434 A1 | 12/2008 | Dobbles et al. |
| 2008/0319383 A1 | 12/2008 | Byland et al. |
| 2009/0054750 A1 | 2/2009 | Jennewine |
| 2009/0058823 A1 | 3/2009 | Kocienda |
| 2009/0067989 A1 | 3/2009 | Estes et al. |
| 2009/0069745 A1 | 3/2009 | Estes et al. |
| 2009/0069746 A1 | 3/2009 | Miller et al. |
| 2009/0069749 A1 | 3/2009 | Miller et al. |
| 2009/0069784 A1 | 3/2009 | Estes et al. |
| 2009/0069785 A1 | 3/2009 | Miller et al. |
| 2009/0069787 A1 | 3/2009 | Estes et al. |
| 2009/0089710 A1 | 4/2009 | Wood et al. |
| 2009/0099523 A1 | 4/2009 | Grant et al. |
| 2009/0156990 A1 | 6/2009 | Wenger et al. |
| 2009/0164239 A1 | 6/2009 | Hayter et al. |
| 2009/0197635 A1 | 8/2009 | Kim et al. |
| 2009/0204421 A1 | 8/2009 | Guimaraes |
| 2009/0253970 A1* | 10/2009 | Bashan .................. G16H 20/17 600/316 |
| 2009/0292247 A1 | 11/2009 | Basso et al. |
| 2010/0016700 A1 | 1/2010 | Sieh et al. |
| 2010/0048358 A1 | 2/2010 | Tchao et al. |
| 2010/0118037 A1 | 5/2010 | Sheikh et al. |
| 2010/0174266 A1 | 7/2010 | Estes |
| 2010/0273610 A1 | 10/2010 | Johnson |
| 2010/0280329 A1 | 11/2010 | Randloev et al. |
| 2010/0286601 A1 | 11/2010 | Yodfat et al. |
| 2010/0298765 A1 | 11/2010 | Budiman et al. |
| 2010/0305965 A1 | 12/2010 | Benjamin et al. |
| 2010/0315359 A1 | 12/2010 | Seong et al. |
| 2011/0009846 A1 | 1/2011 | Istoc et al. |
| 2011/0040247 A1 | 2/2011 | Mandro et al. |
| 2011/0092788 A1 | 4/2011 | Long et al. |
| 2011/0152657 A1 | 6/2011 | Bielawa et al. |
| 2011/0160555 A1 | 6/2011 | Reifman et al. |
| 2011/0201911 A1 | 8/2011 | Johnson et al. |
| 2011/0238520 A1 | 9/2011 | Selley |
| 2011/0273388 A1 | 11/2011 | Joo et al. |
| 2011/0313349 A1 | 12/2011 | Krulevitch et al. |
| 2011/0319322 A1 | 12/2011 | Bashan et al. |
| 2012/0022496 A1 | 1/2012 | Causey et al. |
| 2012/0053560 A1 | 3/2012 | Kawamura |
| 2012/0159328 A1 | 6/2012 | Millington et al. |
| 2012/0215201 A1 | 8/2012 | Brauker et al. |
| 2012/0226124 A1 | 9/2012 | Blomquist |
| 2012/0232520 A1 | 9/2012 | Sloan et al. |
| 2012/0238999 A1 | 9/2012 | Estes et al. |
| 2012/0330270 A1 | 12/2012 | Colton |
| 2013/0165901 A1 | 6/2013 | Ruchti et al. |
| 2013/0172710 A1 | 7/2013 | Mears et al. |
| 2013/0184547 A1* | 7/2013 | Taub .................. A61B 5/14532 600/365 |
| 2013/0245545 A1 | 9/2013 | Arnold et al. |
| 2013/0318439 A1 | 11/2013 | Landis et al. |
| 2013/0324941 A1 | 12/2013 | Mann et al. |
| 2013/0331659 A1 | 12/2013 | Koski et al. |
| 2013/0332952 A1 | 12/2013 | Anandpura et al. |
| 2013/0338453 A1 | 12/2013 | Duke et al. |
| 2014/0012117 A1 | 1/2014 | Mensinger et al. |
| 2014/0025400 A1 | 1/2014 | Galley et al. |
| 2014/0031786 A1 | 1/2014 | Kircher, Jr. et al. |
| 2014/0039383 A1 | 2/2014 | Dobbles et al. |
| 2014/0058749 A1 | 2/2014 | Galley et al. |
| 2014/0068487 A1 | 3/2014 | Steiger et al. |
| 2014/0073892 A1 | 3/2014 | Randloev et al. |
| 2014/0154987 A1 | 6/2014 | Lee et al. |
| 2014/0160078 A1 | 6/2014 | Seo et al. |
| 2014/0309615 A1 | 10/2014 | Mazlish |
| 2014/0317546 A1 | 10/2014 | Jacobson et al. |
| 2014/0344280 A1 | 11/2014 | Wei et al. |
| 2014/0358082 A1 | 12/2014 | Ohzawa |
| 2014/0380218 A1 | 12/2014 | Johnnie |
| 2015/0025498 A1 | 1/2015 | Estes |
| 2015/0067527 A1 | 3/2015 | Gardner et al. |
| 2015/0073337 A1 | 3/2015 | Saint et al. |
| 2015/0073754 A1* | 3/2015 | Okkonen ............... G16H 50/30 703/2 |
| 2015/0080842 A1 | 3/2015 | Mathys |
| 2015/0112264 A1 | 4/2015 | Kamen et al. |
| 2015/0141912 A1 | 5/2015 | Estes |
| 2015/0173674 A1 | 6/2015 | Hayes et al. |
| 2015/0277722 A1 | 10/2015 | Masterson et al. |
| 2016/0000998 A1 | 1/2016 | Estes |
| 2016/0038675 A1 | 2/2016 | Estes et al. |
| 2016/0058939 A1 | 3/2016 | Brewer et al. |
| 2016/0072841 A1 | 3/2016 | Caporal et al. |
| 2016/0089491 A1 | 3/2016 | Smith |
| 2016/0110064 A1 | 4/2016 | Shapira |
| 2016/0139671 A1 | 5/2016 | Jun et al. |
| 2016/0235913 A1 | 8/2016 | Smith et al. |
| 2016/0250422 A1 | 9/2016 | Koch et al. |
| 2016/0317743 A1* | 11/2016 | Estes ..................... G16H 20/17 |
| 2016/0357371 A1 | 12/2016 | Lee |
| 2016/0361494 A1 | 12/2016 | Jurg et al. |
| 2017/0003848 A1 | 1/2017 | Wakayanagi et al. |
| 2017/0017374 A1 | 1/2017 | Herz |
| 2017/0049957 A1 | 2/2017 | Michaud |
| 2017/0056591 A1 | 3/2017 | Breton et al. |
| 2017/0100538 A1 | 4/2017 | Mhatre et al. |
| 2017/0165416 A1 | 6/2017 | Saint |
| 2017/0173262 A1 | 6/2017 | Veltz |
| 2017/0176952 A1 | 6/2017 | Misaki et al. |
| 2017/0189614 A1 | 7/2017 | Mazlish et al. |
| 2017/0193184 A1 | 7/2017 | Hayter et al. |
| 2017/0199985 A1 | 7/2017 | Mazlish et al. |
| 2017/0203030 A1 | 7/2017 | Brewer et al. |
| 2017/0203036 A1 | 7/2017 | Mazlish et al. |
| 2017/0203037 A1 | 7/2017 | Desborough et al. |
| 2017/0203038 A1 | 7/2017 | Desborough et al. |
| 2017/0203039 A1 | 7/2017 | Desborough et al. |
| 2017/0216524 A1 | 8/2017 | Haider et al. |
| 2017/0224910 A1 | 8/2017 | Yodfat et al. |
| 2017/0232195 A1 | 8/2017 | Desborough et al. |
| 2017/0242975 A1 | 8/2017 | Kahlbaugh |
| 2017/0255771 A1 | 9/2017 | Miyakawa |
| 2017/0316592 A1 | 11/2017 | Kamath et al. |
| 2017/0332952 A1 | 11/2017 | Desborough et al. |
| 2017/0348484 A1* | 12/2017 | Duke ..................... G16H 20/17 |
| 2017/0351842 A1 | 12/2017 | Booth et al. |
| 2018/0001006 A1 | 1/2018 | Schade et al. |
| 2018/0036495 A1 | 2/2018 | Searle et al. |

(56) References Cited

U.S. PATENT DOCUMENTS

| | | | |
|---|---|---|---|
| 2018/0089395 A1 | 3/2018 | Desborough et al. |
| 2018/0101297 A1 | 4/2018 | Yang et al. |
| 2018/0133397 A1 | 5/2018 | Estes |
| 2018/0147362 A1 | 5/2018 | Arenas et al. |
| 2018/0150614 A1 | 5/2018 | Sokolovskyy et al. |
| 2018/0161499 A1 | 6/2018 | Al-Ali et al. |
| 2018/0200435 A1 | 7/2018 | Mazlish et al. |
| 2018/0200436 A1 | 7/2018 | Mazlish et al. |
| 2018/0200437 A1 | 7/2018 | Mazlish et al. |
| 2018/0200438 A1 | 7/2018 | Mazlish et al. |
| 2018/0200439 A1 | 7/2018 | Mazlish et al. |
| 2018/0200441 A1 | 7/2018 | Desborough et al. |
| 2018/0207380 A1 | 7/2018 | Lantz et al. |
| 2018/0361060 A9 | 12/2018 | Rosinko |
| 2019/0001067 A1 | 1/2019 | Berey et al. |
| 2019/0015024 A1 | 1/2019 | Desborough et al. |
| 2019/0175841 A1* | 6/2019 | Sjolund ............... A61B 5/4839 |
| 2019/0183434 A1 | 6/2019 | Sjolund et al. |
| 2019/0184111 A1 | 6/2019 | Sjolund et al. |
| 2019/0265871 A1 | 8/2019 | Eim et al. |
| 2019/0274624 A1 | 9/2019 | Mazlish et al. |
| 2019/0348166 A1 | 11/2019 | Booth et al. |
| 2020/0042166 A1 | 2/2020 | Burns et al. |
| 2020/0097131 A1 | 3/2020 | Bowden et al. |
| 2020/0201494 A1 | 6/2020 | Allington et al. |
| 2020/0236212 A1 | 7/2020 | Vinna et al. |

FOREIGN PATENT DOCUMENTS

| | | |
|---|---|---|
| DE | 19627619 | 1/1998 |
| DE | 10236669 A1 | 2/2004 |
| EM | 000627617-0002 | 1/2007 |
| EM | 000627617-0003 | 1/2007 |
| EM | 000627617-0091 | 1/2007 |
| EM | 0006276170001 | 1/2007 |
| EM | 0006276170002 | 1/2007 |
| EM | 0006276170003 | 1/2007 |
| EM | 000732649-0001 | 6/2007 |
| EM | 000732649-0002 | 6/2007 |
| EM | 0007326490001 | 6/2007 |
| EM | 0007326490002 | 6/2007 |
| EM | 003126705-0091 | 7/2016 |
| EM | 003126795-9992 | 7/2016 |
| EM | 003126795-9993 | 7/2016 |
| EM | 003126795-9994 | 7/2016 |
| EM | 0031267050001 | 7/2016 |
| EM | 0031267050002 | 7/2016 |
| EM | 0031267050003 | 7/2016 |
| EM | 0031267050004 | 7/2016 |
| EP | 0062974 A1 | 10/1982 |
| EP | 0275213 A2 | 7/1988 |
| EP | 0496141 A1 | 7/1992 |
| EP | 0580723 A1 | 2/1994 |
| EP | 0612004 A1 | 8/1994 |
| EP | 0721358 A1 | 7/1996 |
| EP | 1045146 A2 | 10/2000 |
| EP | 1136698 A1 | 9/2001 |
| EP | 1177802 A1 | 2/2002 |
| EP | 1495775 A1 | 1/2005 |
| EP | 1527792 A1 | 5/2005 |
| EP | 1754498 A1 | 2/2007 |
| EP | 1818664 A1 | 8/2007 |
| EP | 2585252 A1 | 5/2013 |
| FR | 2585252 A1 | 1/1987 |
| GB | 0747701 | 4/1956 |
| GB | 2218831 A | 11/1989 |
| WO | 90/15928 A1 | 12/1990 |
| WO | 95/09021 A1 | 4/1995 |
| WO | 97/21457 A1 | 6/1997 |
| WO | 98/04301 A1 | 2/1998 |
| WO | 98/11927 A1 | 3/1998 |
| WO | 98/57683 A1 | 12/1998 |
| WO | 99/21596 A1 | 5/1999 |
| WO | 99/39118 A1 | 8/1999 |
| WO | 99/48546 A1 | 9/1999 |
| WO | 01/72360 A1 | 10/2001 |
| WO | 01/91822 A1 | 12/2001 |
| WO | 01/91833 A1 | 12/2001 |
| WO | 02/40083 A2 | 5/2002 |
| WO | 02/57627 A1 | 7/2002 |
| WO | 02/68015 A2 | 9/2002 |
| WO | 02/84336 A2 | 10/2002 |
| WO | 2002/100469 A2 | 12/2002 |
| WO | 03/26726 A1 | 4/2003 |
| WO | 2003/103763 A1 | 12/2003 |
| WO | 2004/056412 A2 | 7/2004 |
| WO | 2004/110526 A1 | 12/2004 |
| WO | 2005/002652 A2 | 1/2005 |
| WO | 2005/039673 A2 | 5/2005 |
| WO | 2005/072794 A2 | 8/2005 |
| WO | 2005/072795 A2 | 8/2005 |
| WO | 2006/067217 A2 | 6/2006 |
| WO | 2006/097453 A1 | 9/2006 |
| WO | 2006/105792 A1 | 10/2006 |
| WO | 2006/105793 A1 | 10/2006 |
| WO | 2006/105794 A1 | 10/2006 |
| WO | 2007/141786 A1 | 12/2007 |
| WO | 2011/163450 A1 | 12/2011 |
| WO | 2016/019192 A | 2/2016 |
| WO | 2017/009724 | 1/2017 |

OTHER PUBLICATIONS

Eren-Oruklu et al., Adaptive Control Strategy for Regulation of Blood Glucose Levels in Patients with Type 1 Diabetes, ScienceDirect 2009, pp. 1333-1346. (Year: 2009).*

"Clean Toggle Button Navigation Menu PSD" Jan. 24, 2014, WeLoveSoLo, site visited Oct. 19, 2018: https://www.welovesolo.com/clean-toggle-button-navigation-menu-psd/.

"Omnipod Horizon: Automated Glucose Control" Jun. 2017, 2 pages.

Accu-Chek Spirit, "Pump Therapy Made for You," Roche, 2006, 6 pages.

Arrow Repeat. By Flaticon. Freepik.com. Date: 2014. Retrieved from Internet: <https://www.freepik com/free-icon/arrow-repeat_694329.htm#term=arrows&page=47&position=67> (Year: 2014).

Arrows Curves Forming an Oval Shape. By Flaticon. Freepik.com. Date: 2015. Retrieved from Internet: <https://www.freepik.com/free-icon/arrows-curves-forming-an-oval-shape_746143.htm> (Year: 2015).

Arrows, Couple, IOS 7 Interface Symbol. By Flaticon. Freepik.com. Date: 2015. Retrieved from Internet: <https://www.freepik.com/free-icon/arrows-couple-ios-7-interface-symbo_751266.htm#tterm=arrows&page=68&position=43> (Year: 2015).

Baruah, Insulin Pens: The Modern Delivery Devices, Google Scholar 2011, pp. 38-40. (Year: 2011).

Bhalla, Raveesh, Understanding Material Design Part II, Sep. 28, 2014, Medium.com [online], [site visited Apr. 11, 2018], Available from Internet: https://medium.eom/@raveeshbhalla/understanding-material-design-cf2d60a16de3 (Year: 2014).

Bigfoot Biomedical Reveals its Automated Insulin Delivery System. diaTribe. Date published: Jan. 25, 2016 <https://diatribe.org/bigfoot-biomedical-reveals-its-automated-insulin-delivery-system>.

Bode et al., Diabetes Management in the New Millennium Using Insulin Pump Therapy, Wiley Inter Science 2002, pp. 514-520. (Year: 2002).

Collins and Lee, "Microfluidic flow transducer based on the measurement of electrical admittance," Lab Chip, 2004,4:7-10.

Curved Arrow to the Right. By Flaticon. Freepik.com. Date: 2015. Retrieved from Internet: 21 https://www.freepik.com/free-icon/curved-arrow-to-the-right 735735.htm#term=arrows&page=59&position=69> (Year: 2015).

Dassau and Associates, 12-Week 24/7 Ambulatory Artificial Pancreas With Weekly Adaptation of Insulin Delivery Settings: Effect on Hemoglobin A1C and Hypoglycemia, Diabetes Care, Oct. 13, 2017.

David A. Copp, Ravi Gondhalekar, and Joao P. Hespanha, Simultaneous Model Predictive Control and Moving Horizon Estimation

(56) References Cited

OTHER PUBLICATIONS for Blood Glucose Regulation in Type 1 Diabetes, Optimal Control Applications and Methods, Wiley InterScience, DOI: 10.1002/oca, pp. 1-15, Oct. 2016.
Delaney, Chelsey, "4 apps for tracking your fertility" Jun. 6, 2016, Bedsider, site visited Oct. 19, 2018: https://www.bedsider.org/features/647-4-apps-for-tracking-your-fertility.
Dreyfuss, Henry. Symbol Sourcebook. Van Nostrand Reinhold Company. Date published: 1984. Page 28. (Year: 1984).
E. Salzsieder, G. Albrecht, E. Jutzi, and U. Fischer, Estimation of Individually Adapted Control Parameten for an Artificial Beta Cell, Biomedica Biochimica Acta. 43(5) pp. 585-596, May 1984.
Fischer et al.. In Vivo Comparison of Different Algorithms for the Artificial Beta-Cell, Artificial Organs, 9(2), International Society for Artificial Organs, May 1985, New York.
Guy A. Dumont, Feedback Control for Clinicians, Springer Science+ Media, Apr. 12, 2013, New York.
Hoskins, Mike, NEWS: Bigfoot Closed Loop, Jul. 17, 2017, Healthline.com [online], [visited Jan. 22, 2019]. Internet: https://web.archive.org/web/20170810052840/https://www.diabetesdaily.com/blog/bigfoot-biomedical-aims-to-take-multiple-daily-injections-to-the-next-level-with-timesulin-acquisition (Year: 2017).
International Search Report for PCT Application No. PCT/US2017/053814, dated Jan. 4, 2018, 4 pages.
Kuwayama, Yasaburo. Trademarks & Symbols. vol. 2: Symbolical Designs. Van Nostrand Reinhold Company. Date published: 1973. p. 136 (Year: 1973).
Michele Schiavon, Chiara Dalla Man, Yogish C. Kudva, Ananda Basu, and Claudio Cobelli, Quantitative Estimation of Insulin Sensitivity in Type 1 Diabetic Subjects Wearing a Sensor-Augmented Insulin Pump, Diabetes Care, vol. 37, pp. 1216-1223, May 2014.
OmniPod Insulin Management System—Investor Relations—Press Release, Feb. 1, 2005, http://investors.insulel.com/phoenix.zhlml?c=209336&p=irol-newsArticle&ID=988708&highlight= 1 page.
OmniPod Quick Start Guide, 2007, 2 pages.
Patent Abstracts of Japan, vol. 1999, No. 04, and JP 11 010036, Apr. 30, 1999 and Jan. 19, 1999, Toray Ind. Inc.
Pearson, Practical Aspect of Insulin Pen Devices, Journal of Diabetes Science and Technology 2010, pp. 522-531. (Year: 2010).
Refresh Arrow Loop. By Flaticon. Freepik.com. Date:2014. Retrieved from Internet: <https://www.freepik.com/free-icon/refresh-arrow-loop_705291.htm#term=arrows&page=49&position=43> (Year: 2014).
Refreshing. By Flaticon. Freepik.com. Date: 2016. Retrieved from Internet: <https://www.freepik.com/free-icon/refreshing_807573.htm#term=arrows&page=26&position=26> (Year: 2016).
Sara Krugman, Bionic Pancreas User Interface (3/4): Interface Details, Tidepool.org, Jul. 20, 2015.
Sindaco et al., Use of the Short-acting Insulin Analogue Lispro in Intensive Treatment of Type 1 Diabetes Mellitus: Importance of Appropriate Replacement of Basal Insulin and Time-interval Injection-meal, Diabetic Medicine 1998, pp. 592-600. (Year: 1998).
Smart et al., "Can children with type 1 diabetes and their caregivers estimate the carbohydrate content of meals and snacks?" Diabetic Medicine, 27, No. 3 (2010) pp. 38-353.
Synchronise, IOS 7 Interface Symbol. By Flaticon. Freepik.com. Date: 2015. Retrieved from Internet: <https://www.freepik.com/free-icon/synchronise-ios-7-interface-symbol_751804.htm#term=arrows&page=69&position=14> (Year: 2015).
T:slimx2 Insulin Pump User Guide, Tandem Diabetes Care, Jul. 22, 2016.
The Medtronic Diabetes Connection, 2006, 6 pages.
Written Opinion of the International Searching Authority for PCT Application No. PCT/US2017/053814, dated Jan. 4, 2018, 8 pages.
Xilas Temp Touch, "The latest in high-tech and convenient devices," DOCNews, vol. 2, No. 7, Jul. 1, 2005, http://docnews.diabetesjoumals.ordlcgi/contenl/foll/2/7i 13, 3 pages.
Zhang et al., Second Insulin Pump Safety Meeting: Summary Report, Journal of Diabetes Science and Technology 2010, pp. 488-493. (Year: 2010).

"Medical Set." iconfinder.com. Added Apr. 7, 2017. Accessed Jan. 27, 2020. Available online at URL: https://www.iconfinder.com/iconsets/medical-set-5 (Year: 2017).
"Three icons—Ready, Set and Go" Nov. 29, 2015, depositphotos, site visited Apr. 21, 2020: https://depositphotos.com/91436542/stock-illustration-countdown-ready-set-go-colorful.html (Year: 2015).
Ansyari, Nazurrudin. "Circle Badge Set." iconfinder.com. Added Aug. 15, 2016. Accessed Jan. 27, 2020. Available online at URL: https://www.iconfinder.com/iconsets/ciicle-badge-set (Year: 2016).
Bhalla, Reveesh, Understading Material Design Part II, Sep. 28, 2014, Medium.com [online], [site visited Apr. 11, 2018], Available from Internet: https://medium.com/@raveeshbhalla/understanding-material-design-cf2d60a16de3 (Year: 2014).
Bigfoot Biomedical Reveals its Automated Insulin Delivery System. diaTribe. Date published: Jan. 25, 2016 <https://diatrive.org/bigfoot-biomedical-reveals-its-automated-insulin-delivery-system>.
Centers for Disease Control and Prevention, Number (in Millions) of Adults with Diabetes by Diabetes Medication Status, United States, 1997-2011, http://www.cdc.gov/diabetes/statislics/meduse/fig1.him, 2013.
Debiotech News Release, "Debiotech reveals its new miniaturized Disposable Insulin Nanopump™ for Diabetes therapy," available at http://www.debiotech.com/news/nw 159.html Apr. 24, 2006, 3 pages.
European Search Report and Opinion for European Application No. 17857364.8, dated Apr. 21, 2020, 8 pages.
Grill et al., Exercise and Postprandial Lipid Metabolism: an Update on Potential Mechanisms and Interactions with High-Carbohydrate Diets/(Review), Elsevier 2003, pp. 122-132. (Year: 2003).
Harvey et al., Quest for the Artificial Pancreas, IEEE 2010, pp. 53-62. (Year: 2010).
Hurley, Dan. Artificial Pancreas Makers Race to Markel. Discover. Date published: Apr. 12, 2016. <http://discovermagazine.com/2016/may/13-priming-the-pump>.
JDRF, Statistics: JDRF and Diabetes, http://jdrf.org/aboul-jdrf/facl-sheels/jdrf-anddiabeles- statistics/, 2014.
Karnes, Chris. "Kids Mental Health App." dribbble.com. Feb. 1, 2020. Accessed May 7, 2020. Available online at URL: https://dribbble.com/shots/9841070-Kids-Mental-Health-App (Year: 2020).
Kumar, Rohit. "Health App." dribbble.com. May 14, 2015. Accessed May 7, 2020. Available online at URL: https://dribbble.com/shots/2062723-Health-App (Year: 2015).
Medtronic News Release, "Medtronic Receives FDA Approval for World's First Insulin Pump with Real-time Continuous Glucose Monitoring," Apr. 13, 2006, 3 pages.
Samuel Vozeh and Jean-Louis Steimer, Feedback Control Methods for Drug Dosage Optimisation, Concepts, Classification and Clinical Application, Clinical Pharmacokinetics, 10(6), pp. 457-476, Nov.-Dec. 1985.
Shishir, Shahidl Islam. "Med-i App | Splash Home and Logo." dribbble.com. Jul. 28, 2019. Accessed May 7, 2020. Available online at URL: https://dribbble.com/shots/6852974-Med-i-App-I-Splash-Home-and-Logo (Year: 2019).
Simmons, Cory, "How to Make Your Own Button UI Kil with Super-Clean Syntax" Dec. 23, 2014, envato tuts+, site visited Sep. 19, 2019: https://webdesign.lutsplus.com/lutorials/how-lo-make-your--0wn-button-ui-kil-wilh-super-clean-syntax-cms-22946.
Australian Examination Report from Australian Application No. 2017335762, dated Oct. 29, 2021, 3 pages.
Dreyfuss, Henry. Symbol Sourcebook: An Authoritative Guide to International Graphic Symbols. Van Nostrand Reinhold, 1984. p. 52. (Year: 1984).
U.S. Trademark Serial No. 85698749 to Mmillenniumm Group Ing. Filed Aug. 8, 2012. Retrieved Mar. 7, 2022 online via Trademark Electronic Search System (TESS). (Year: 2012).
U.S. Trademark Serial No. 86854669 to DynoSense Corp. Filed Dec. 19, 2015. Retrieved Mar. 7, 2022 online via Trademark Electronic Search System (TESS). (Year: 2015).
Chinese First Office Action for Chinese Application No. 201910969068.3 dated Nov. 21, 2022, 13 pages with translation.
European Communication pursuant to Article 94(3) EPC for European Application No. 17857362.2, dated Mar. 20, 2023, 5 pages.

(56) References Cited

OTHER PUBLICATIONS

"LifeScan Receives FDA Clearance for One Touch VerioSync Bluetooth Blood Glucose Meter" Mar. 7, 2013, posted at medgadget.com, [site visited May 30, 2023]. https://www.medgadget.com/2013/03/lifescan-receives-fda-clearance-for-onetouch-veriosync-bluetooth-blood-glucose-meter.html (Year: 2013).

"SeebeckCell Technologies" Jul. 7, 2022, posted at greentownlabs.com, [site visited May 30, 2023]. https://web.archive.org/web/20220707134432/https://greentownlabs.com/members/seebeckcell-technologies (Year: 2022).

* cited by examiner

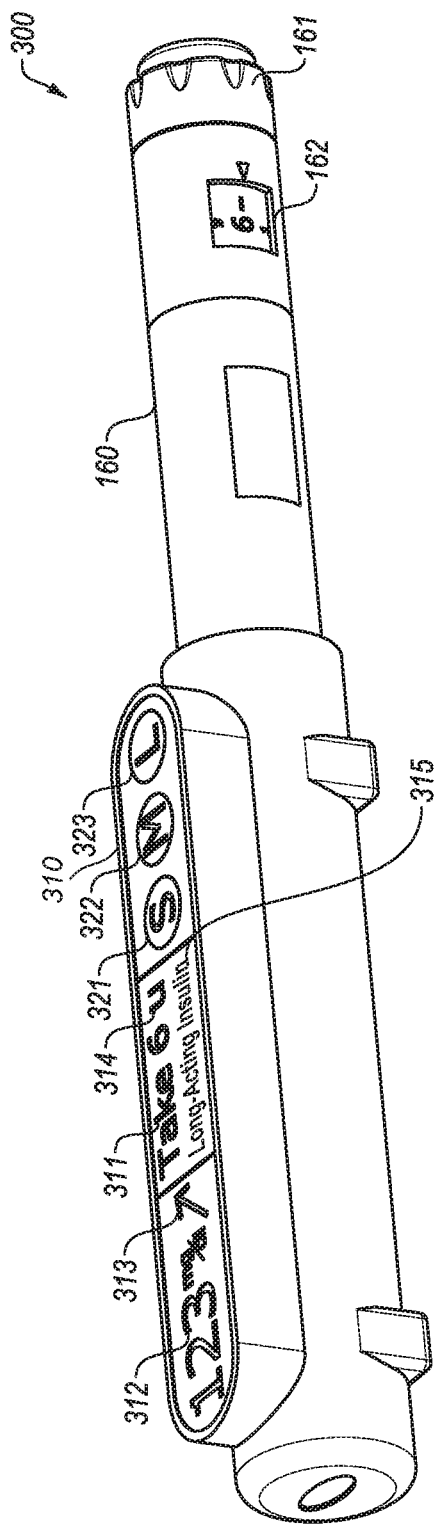
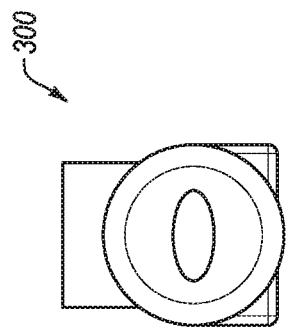
FIG. 3A
FIG. 3B

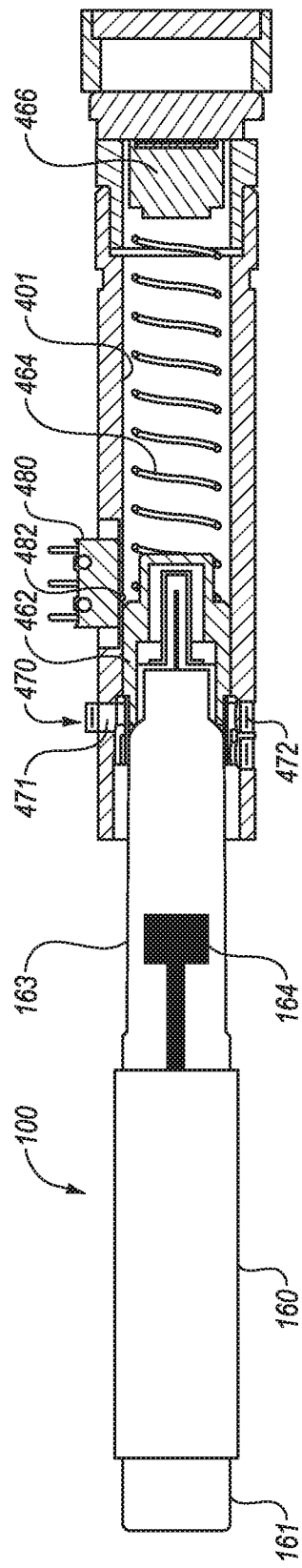
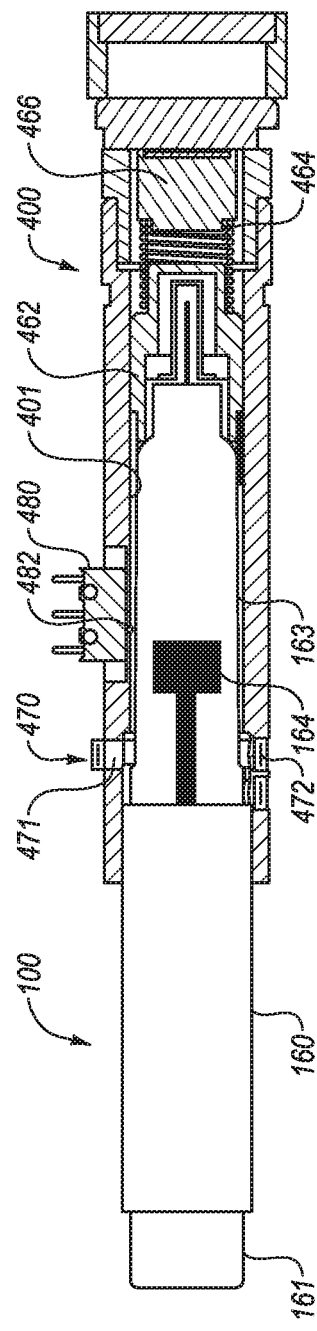

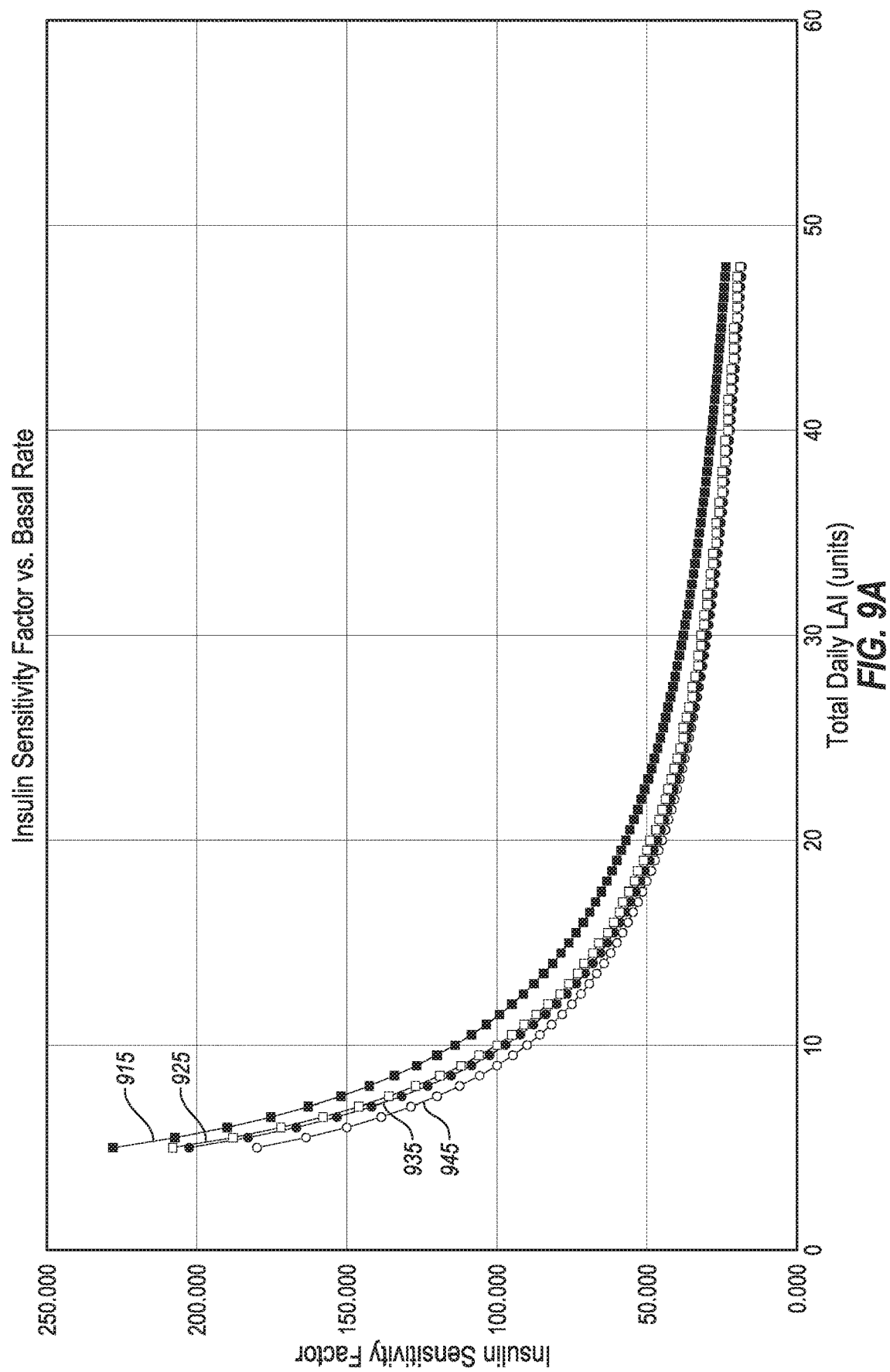

MEDICINE INJECTION AND DISEASE MANAGEMENT SYSTEMS, DEVICES, AND METHODS

CROSS-REFERENCE TO RELATED APPLICATIONS

This application is a continuation of U.S. patent application Ser. No. 15/717,805, filed Sep. 27, 2017, now U.S. Pat. No. 10,426,896, issued Oct. 1, 2019, which claims the benefit of U.S. Patent Provisional Application No. 62/400,366, filed Sep. 27, 2016, the disclosure of each of which is hereby incorporated herein in its entirety by this reference.

TECHNICAL FIELD

The present disclosure relates to medicine injection and disease management systems, devices, and methods, particularly those related to the management of diabetes and/or the delivery of insulin. In some embodiments, systems, methods, and devices provided herein can personalize user-selectable meal sizes for a user to enter meal data for purposes of obtaining recommendations regarding one or more medication doses. In some cases, one or more buttons (e.g., user-selectable icons, physical press buttons, etc.) can be personalized to describe an amount or range of amounts of insulin to be delivered and/or carbohydrates to be consumed.

BACKGROUND

Diabetes mellitus is a chronic metabolic disorder caused by an inability of a person's pancreas to produce sufficient amounts of the hormone, insulin, such that the person's metabolism is unable to provide for the proper absorption of sugar and starch. This failure leads to hyperglycemia, i.e., the presence of an excessive amount of analyte, such as glucose, within the blood plasma. Persistent hyperglycemia has been associated with a variety of serious symptoms and life threatening long-term complications such as dehydration, ketoacidosis, diabetic coma, cardiovascular diseases, chronic renal failure, retinal damage and nerve damages with the risk of amputation of extremities. Self-monitoring of blood glucose and the self-administration of insulin is the typical method for treating diabetes. The "correct" insulin dosage is a function of the level of glucose in the blood. Insufficient insulin dosages can result in hyperglycemia, and excessive insulin dosages can result in hypoglycemia, which can result in clumsiness, trouble talking, confusion, loss of consciousness, seizures, or death. Accordingly, people with diabetes (PWDs) face a considerable cognitive burden in determining an appropriate dosage of insulin.

In order to assist with this self-treatment, many diabetes-related devices (e.g., blood glucose meters, insulin pumps, etc.) are equipped with insulin bolus calculators that have the user input a number of carbohydrates consumed (or about to be consumed) and the bolus calculator outputs a recommended size for the insulin bolus dosage. Although bolus calculators remove some of the calculations that need to be made by the user in determining an appropriate insulin bolus dosage, bolus calculators still burden the user with the mental task of determining the number of carbohydrates in their meal and often require manual entry of data. Accordingly, there is a need for methods, systems, and devices that further reduce the cognitive burden on the user while improving the accuracy of a recommended insulin bolus dosage.

BRIEF SUMMARY

Systems, devices and methods provided herein can be equipped to simplify calculation of a recommended insulin dosage by simplifying a meal announcement process and/or simplifying the collection of an estimated glucose value (EGV). A meal announcement process can be simplified by providing a user interface that includes one or more meal announcement buttons, which can be user-selectable icons on a touchscreen, physical press buttons, jog dials, voice activation commands, etc. In some cases, meal announcement buttons can be located on part of an insulin delivery device or on an accessory for an insulin delivery device. In some cases, the insulin delivery device can be an insulin pen and a dose capture pen cap including the meal announcement buttons. In some cases, an insulin delivery device or an accessory therefor can be in wireless communication with a remote user interface device (e.g., a mobile application on a smartphone) and the meal announcement buttons can be on the remote user interface device (either as physical press buttons or as user-selectable icons on a touch screen). The one or more meal announcement buttons can be personalized based on user's use of the system. Such personalization may be based on a user interacting with various buttons or features (e.g., the user selecting various meal sizes for boluses), by providing boluses and measuring the effect for the boluses over time, or any other use of devices or systems in accordance with the present disclosure.

One or more embodiments of the present disclosure may include an insulin delivery system that includes an insulin delivery device, a user interface that includes multiple user-selectable icons or buttons each representing different meal characteristics, memory to store one or more user-specific dosage parameter, and a processor in communication with the memory and adapted to receive blood glucose data. The processor may also be adapted to determine initial meal characteristics associated with each of the user-selectable icons or buttons based on at least one of the user-specific dosage parameters. The processor may also be adapted to update the meal characteristics associated with each of the user-selectable icons or buttons based upon the blood glucose data.

In accordance with one or more devices, systems, or methods of the present disclosure, a device or system may include a blood glucose monitor or sensor.

In accordance with one or more devices, systems, or methods of the present disclosure, the systems or devices may include a flash glucose monitor that includes a flash near field communication circuit, and a system near field communication circuit in communication with the processor. In these and other embodiments, the processor may be adapted to receive the blood glucose data via near field communications (NFC) when the system near field communication circuit and the flash near field communication circuit are brought within an NFC communication distance.

In accordance with one or more devices, systems, or methods of the present disclosure, the systems or devices may include a continuous glucose monitor, and the processor may be adapted to receive wireless communications from the continuous glucose monitor at predetermined time intervals.

In accordance with one or more devices, systems, or methods of the present disclosure, the systems or devices may include a continuous glucose monitor, and the processor may be adapted to receive wireless communications from the continuous glucose monitor at predetermined time intervals.

In accordance with one or more devices, systems, or methods of the present disclosure, the user-selectable icons or buttons may each initially represent an amount of carbohydrates in 5 gram or 10 gram increments.

In accordance with one or more devices, systems, or methods of the present disclosure, the amount of carbohydrates initially represented by each of the plurality of icons may be determined based on an insulin Sensitivity Factor (ISF), a Carb Ratio (CR), a body weight, an age, a total daily basal (TDB) rate, a daily dosage of Long-Acting Insulin, a weight averaged total daily dosage (TDD) of insulin and/or a combination thereof of a person with diabetes (PWD).

In accordance with one or more devices, systems, or methods of the present disclosure, the processor may be further configured to determine an insulin delivery amount based on an amount of carbohydrates associated with a selected one of the user-selectable icons or buttons and/or the blood glucose data.

In accordance with one or more devices, systems, or methods of the present disclosure, the user-selectable icons or buttons may each represent a number of units of insulin that are needed to compensate for each meal, rounded to the nearest 0.5 units.

In accordance with one or more devices, systems, or methods of the present disclosure, the updating of the meal characteristics associated with each of the plurality of user-selectable icons or buttons may be determined from postprandial blood glucose data after the user has selected a given user-selectable icon or button.

In accordance with one or more devices, systems, or methods of the present disclosure, the systems or devices may include a flash glucose monitor that includes a flash near field communication circuit, and the systems or devices may further include one or more system near field communication circuits in communication with the processor. In these and other cases, the processor may be adapted to receive the postprandial blood glucose data via near field communications (NFC) when the one or more system near field communication circuits and the flash near field communication circuit are brought within an NFC communication distance. Additionally, the processor may be adapted to send a prompt to the user to retrieve the postprandial blood glucose data by bringing one of the one or more system near field communication circuits into close proximity to the flash glucose monitor at a predetermined time after insulin is delivered or one of the user-selectable icons or buttons has been selected by the user.

In accordance with one or more devices, systems, or methods of the present disclosure, the user interface may be adapted to display a bolus recommendation based on the blood glucose data and a selection of one of the user-selectable icons or buttons.

In accordance with one or more devices, systems, or methods of the present disclosure, the processor may determine the bolus recommendation based on factors selected from the number of carbohydrates divided by the PWD's carbohydrate-to-insulin ratio, a difference between the current blood glucose level and a target blood glucose level divided by the PWD's insulin sensitivity factor, a reading from a blood glucose meter (BGM), data from a continuous glucose monitor (CGM), blood glucose trend data, Insulin on Board (IOB) data, Carbohydrates on Board (COB) data, whether the PWD is or plans to exercise, whether the PWD is sick, whether the PWD is pregnant, whether the PWD is experiencing menses, and whether the PWD has consumed certain medications.

In accordance with one or more devices, systems, or methods of the present disclosure, the processor may be further adapted to receive dosage data from the insulin delivery device, and the update the meal characteristics associated with each of the user-selectable icons or buttons may be based upon postprandial blood glucose data after the user has selected that user-selectable icon or button, the dosage data, or a combination thereof.

In accordance with one or more devices, systems, or methods of the present disclosure, the insulin delivery device may include an insulin pen, and the user interface may be part of the insulin pen, part of a pen accessory adapted to reversibly connect to an insulin pen, or part of a mobile application for a smartphone in wireless communication with an insulin pen or an accessory therefore. In these and other embodiments, the devices or systems may be adapted to detect amounts of insulin remaining in or delivered by one or more insulin pens.

In accordance with one or more devices, systems, or methods of the present disclosure, the pen accessory may be adapted to reversibly connect to an insulin pen, where the pen accessory may include a pen cap that is adapted to detect amounts of insulin remaining in an insulin pen during placement or removal from the insulin pen or when secured to the insulin pen.

In accordance with one or more devices, systems, or methods of the present disclosure, the user interface may be located on the mobile application for a smartphone, where the smartphone further includes the processor, and the insulin pen or an accessory therefor is adapted to detect insulin amount or delivery data and wirelessly communicate the insulin amount or delivery data to the processor.

One or more embodiments of the present disclosure may include a cap for an insulin pen that includes one or more sensors adapted to detect the position of a plunger within an insulin pen, and a user interface that includes one or more user-selectable icons or buttons adapted to announce a meal or an intent to have a meal.

In accordance with one or more devices, systems, or methods of the present disclosure, the cap may include a processor and memory, where the processor may be adapted to determine a time and dosage for an insulin delivery based on data from the one or more sensors and store that information in the memory.

In accordance with one or more devices, systems, or methods of the present disclosure, the user interface may include at least 2, and no more than 6, user-selectable icons or buttons adapted to announce a meal or an intent to have a meal, each representing different meal characteristics stored for each button in the memory.

In accordance with one or more devices, systems, or methods of the present disclosure, the user interface may include a display adapted to display a recommended dosage based at least in part on a selection of the one or more user-selectable icons.

In accordance with one or more devices, systems, or methods of the present disclosure, the cap may include a wireless communication device adapted to communicate with a blood glucose monitor or sensor, where the display may be adapted to display a current blood glucose level, an indication of a current rate of change, a recommended correction bolus dosage based on glucose data, or a combination thereof.

In accordance with one or more devices, systems, or methods of the present disclosure, a wireless communication device of a cap may include an NFC circuit.

In accordance with one or more devices, systems, or methods of the present disclosure, the devices or systems may include an annunciator adapted to prompt the user to obtain blood glucose data from the blood glucose monitor or sensor at a predetermined time after the selection of the one or more user-selectable icons or buttons.

In accordance with one or more devices, systems, or methods of the present disclosure, the devices or systems may include an annunciator adapted to provide an alarm when data from a blood glucose monitor or sensor indicates a need to provide therapy.

In accordance with one or more devices, systems, or methods of the present disclosure, the systems or devices may include a processor and memory, the memory storing meal characterizations for each of the one or more user-selectable icons or buttons, and the processor being adapted to receive blood glucose data and update the meal characterizations for each of the one or more user-selectable icons or buttons based on the blood glucose data.

In accordance with one or more devices, systems, or methods of the present disclosure, the systems or devices may include memory that can store multiple meal characterizations for a single user-selectable icon or button based on the time of day.

In accordance with one or more devices, systems, or methods of the present disclosure, the systems or devices may include a cap that further includes a sensor adapted to detect a characterization of an insulin pen or a type of insulin in an insulin pen, a memory to store information about different types of insulin pens or different types of insulin, and a processor to determine the type of insulin pen or the type of insulin.

In accordance with one or more devices, systems, or methods of the present disclosure, the systems or devices may include a processor adapted to change the user interface dependent on the type of insulin pen or the type of insulin, where some types of insulin or insulin pens result in a user-interface that does not include any user-selectable icons or buttons adapted to announce a meal or an intent to have a meal.

BRIEF DESCRIPTION OF THE DRAWINGS

FIGS. 3A and 3B depict an insulin pen with a second exemplary insulin pen cap having some of the features disclosed herein.

FIGS. 5A and 5B depict an exemplary dose capture technique, which can be incorporated into the pen caps of FIGS. 2A-3B.

FIGS. 9A and 9B are charts illustrating how meal characterizations and user-specific dosage parameters can be initiated or updated.

DETAILED DESCRIPTION

Insulin delivery systems and devices, and methods for delivering insulin, can be designed to minimize the cognitive and active burden for people with diabetes (PWDs), or their caregivers, as they decide to administer insulin. In some embodiment's, methods, systems, and devices provided herein can passively capture diabetes-relevant data (e.g., insulin delivery data, blood glucose data, etc.) with or without providing the PWD (or a caregiver) with recommendations. In some embodiments, methods, systems, and devices provided herein can provide guidance regarding an appropriate dosage of insulin. In some embodiments, the dosage of insulin can be administered with an insulin delivery pen or syringe. In some cases, the insulin can be a long-acting insulin. In some cases, the insulin can be a quick-acting insulin. In some embodiments, an insulin delivery pen, or accessory therefor (e.g., a cap), can detect an amount of insulin delivered from the pen (or an amount of insulin that was set for delivery). In some cases, an insulin pen, or an accessory therefor, can include a user-interface, which can display data or recommendations to the user and/or permit the user to enter data into the insulin pen or accessory. The following exemplary system includes insulin delivery pens having dose capture pen caps, but alternative embodiments are also envisioned where the functionality disclosed herein is incorporated into other accessories for an insulin delivery pen or the insulin delivery pen itself.

Exemplary Insulin Delivery System

Figure 1A:
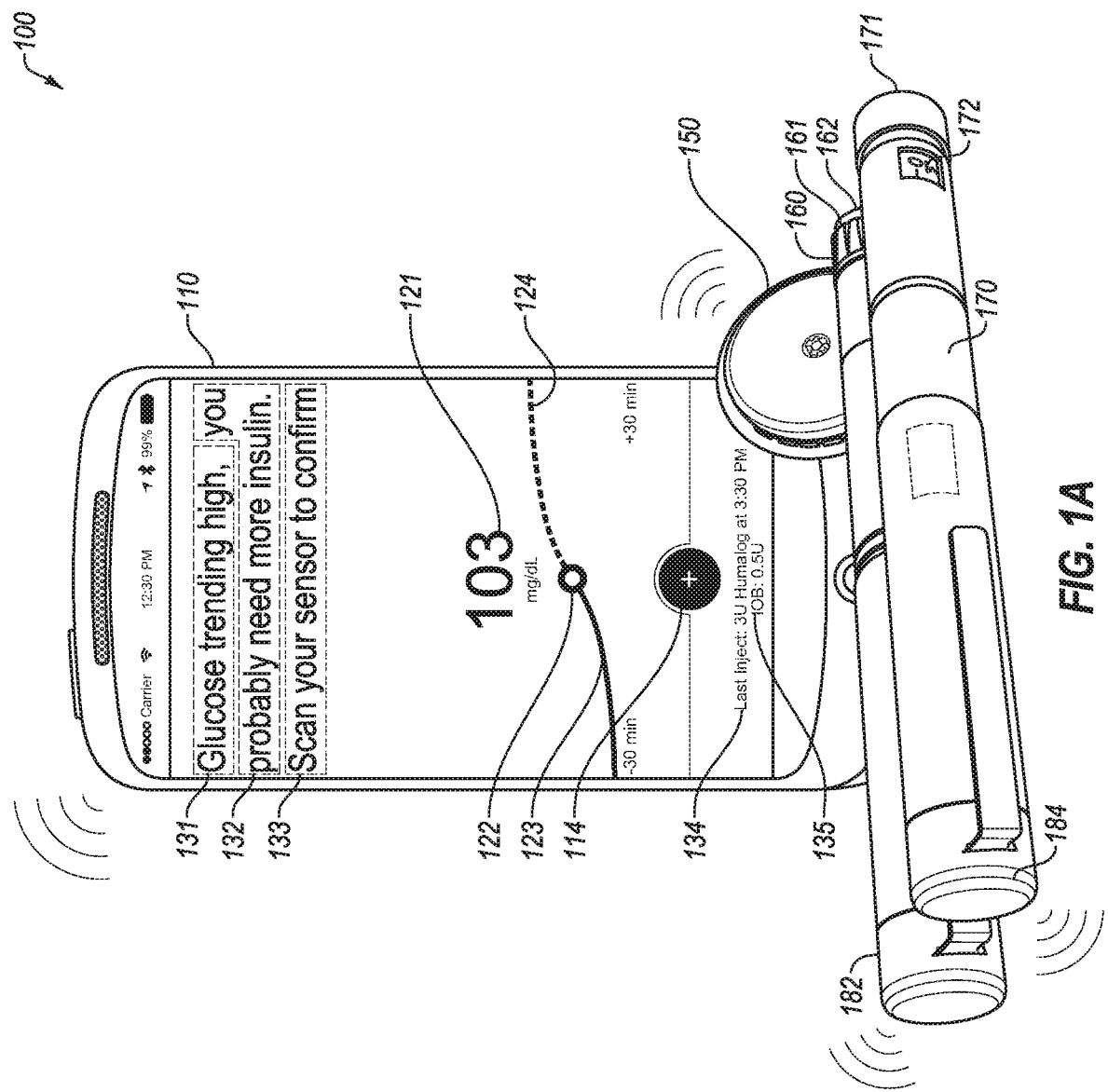
FIG. 1A illustrates a hypothetical insulin delivery system that includes insulin pens, a glucose monitor or sensor, and a remote user interface device having a remote user interface.

FIG. 1A illustrates a hypothetical insulin delivery system 100 that includes a quick-acting insulin (QAI) pen 160 (e.g., HUMALOG™, NOVOLOG™, APIDRA™), a long-acting insulin (LAI) pen 170 (e.g., LANTUSs™, LEVEMIR™, TOUJEO™, TRESIBA™), a glucose monitor or sensor 150, and a remote user interface device 110. As shown, each insulin pen 160 and 170 includes a dose capture cap 182 and 184, respectively, which are in wireless communication with other components of system 100. As shown, the pens can include dials 161 and 171 for a user to set a dosage to be delivered and a dose indicator window 162 and 172. In alternative systems, the insulin pens 160 and/or 170 may themselves include dose capture technology and/or be in wireless communication with other components of system 100. Additional details about possible insulin pens and/or insulin pen caps are disclosed in greater detail below.

Glucose monitor or sensor 150 can be any suitable sensor device and/or monitoring system capable of providing data that can be used to estimate one or more blood glucose values. As shown, glucose monitor or sensor 150 can be a sensor configured to transmit blood glucose data wirelessly. For example, the glucose monitor or sensor 150 can include an optical communication device, an infrared communication device, a wireless communication device (such as an antenna), and/or chipset (such as a BLUETOOTH® device (e.g., BLUETOOTH® Low Energy, Classic BLUETOOTH®, etc.), a Near-field communication (NFC) device, an 802.6 device (e.g., Metropolitan Area Network (MAN), a ZIGBEE® device, etc.), a WiFi device, a WIMAX® device, cellular communication facilities, etc.), and/or the like. The glucose monitor or sensor 150 may exchange data with a network and/or any other devices or systems described in the present disclosure. In some cases, glucose monitor or sensor 150 can be interrogated with an NFC device by the user moving one or more components of the system near the glucose monitor or sensor 150 to power and/or transmit blood glucose data from the glucose monitor or sensor 150 to other components of system 100.

As shown, remote user interface device 110 is a smartphone, but any suitable remote user interface device can be used, such as a computer tablet, a smartphone, a wearable computing device, a smartwatch, a fitness tracker, a laptop computer, a desktop computer, a smart insulin pen (e.g., the dose capture caps 182 and/or 184), and/or other appropriate computing devices. As shown in the exemplary user interface of the exemplary mobile app running on the depicted smartphone, the user interface can include a bolus calculator button 114 and optionally other buttons for the user to enter data or to request recommendations. The exemplary user interface can also include a display of blood glucose data, past, present, or predicted. As shown, the user interface includes a graph of historical data from the previous 30 minutes 123, a continuation of that graph having projected data 124, a point indicator 122 showing the current (or most recent) estimated blood glucose value, and a display of the current (or most recent) estimated blood glucose value 121. The user interface can also include text explaining the glucose data 131, text providing suggested actions 132 and 133, such as text providing insulin, carbohydrates, or other therapy suggestions 132 and/or text suggesting that the user obtain blood glucose data 133. In some cases, the user interface can permit the user to click on the glucose data or otherwise navigate in the mobile app to obtain more detailed or more complete blood glucose data.

The user interface can also depict insulin data. In some cases, the user interface can indicate an amount of Insulin-on-Board (IOB) 135, which may be only for Quick-Acting Insulin. In some cases, an IOB calculation may be for both quick-acting and long-acting insulin. In some cases, the user interface can display the time and/or amounts of the most recent doses of quick-acting and/or long-acting insulins 134. In some cases, the user interface can permit the user to click on the insulin data or otherwise navigate in the mobile app to more detailed or more complete insulin delivery data. In some cases, a user interface can overlay blood glucose data and insulin delivery data in any suitable format, such as a graphical display of the timing of blood glucose data vs. the timing of insulin delivery data.

Figure 1B:
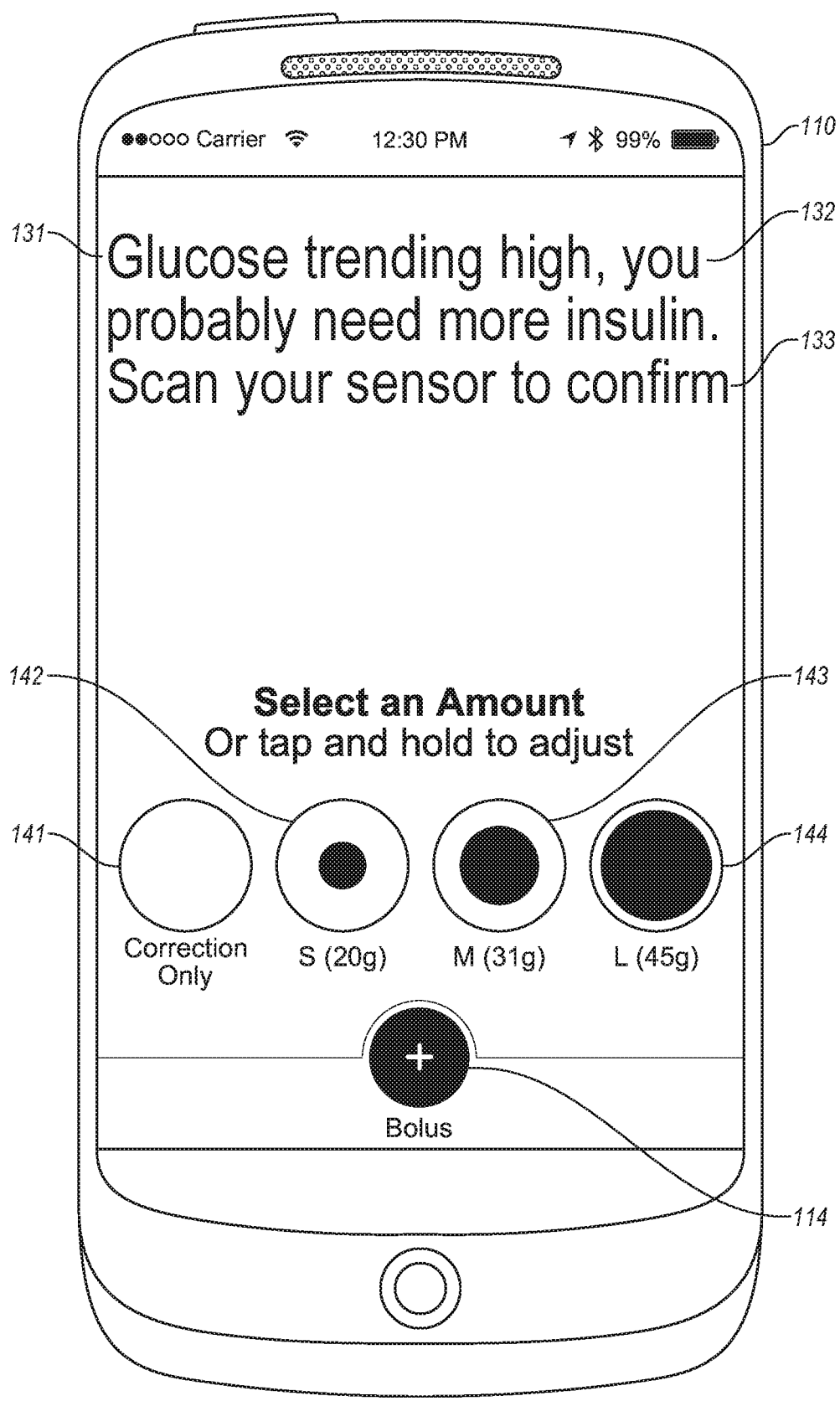
FIG. 1B illustrates an exemplary meal announcement screen for a remote user interface device, which can be displayed by the remote user interface device of FIG. 1A.

In use, a user (e.g., the PWD and/or a caregiver) can use system 100 to get recommendations regarding an appropriate insulin dosage. In the case of an upcoming need to deliver long-acting insulin, the message of 132 may change to provide a recommended long-acting insulin dosage. In some cases, a recommended dosage may appear on pen cap 184. In the case of the user wanting to deliver a bolus of quick-acting insulin, the user may press bolus calculator button 114 to enter into a bolus calculator. Although any suitable bolus calculator could be used in systems, methods, and devices provided herein, FIG. 1B depicts a possible user interface for a user to enter a meal announcement as either a correction only 141, a small meal 142, a normal sized meal 143, or a large meal 144. Upon selecting the meal size, the user interface can provide a recommended bolus dosage based on a number of carbohydrates associated with the corresponding button and optionally based upon blood glucose data.

Additionally, or alternatively, dose capture pen caps for the quick-acting insulin pen 160 can include a user interface that permits the user to announce a small meal, medium meal, or large meal. FIGS. 2A-3B depict possible embodiments of dose capture pen caps 200 and 300 having buttons 221-223 and 321-323 that permit the user to announce a small (S), medium (M), or large (L) meal. In use, a user could announce whether the meal that they just ate or are about to eat is their normal meal size, (M), or larger (L), or smaller (S), and methods, devices, and systems provided herein can determine an appropriate bolus dosage of insulin based on the announcement and optionally based on blood glucose data, if available. Alternatively, an insulin pen can include dose capture technology and include a user interface provided herein and described as being on a dose capture pen cap. In some cases, a smart pen having dose capture capabilities can wirelessly communicate with a remote user interface (e.g., a smartphone).

Personalizing Meal Announcement Buttons

As discussed above, methods, devices, and systems provided herein can provide a user with meal announcement buttons that provide the user with a reduced number of meal size selection options, which can be based upon the user's normal meal size, which can thus reduce the cognitive burden on a user seeking to administer insulin for a meal while improving the accuracy of insulin bolus recommendations. This section describes ways that methods, systems, and devices provided herein can determine an amount of insulin and/or an amount of carbohydrates to associate with each of the meal selection buttons (e.g., 141-144, 221-223, 321-323). Optionally, additional buttons can be present, such as a button that indicates a tiny meal or an extra-large meal for the user, such that any number of buttons are within the scope of the present disclosure. Additionally or alternatively, the system may include a single button, icon, or mode for announcing a meal to systems or devices of the present disclosure.

In some cases, each of the meal announcement buttons 142-144, 221-223, 321-323 can be associated with a number of carbohydrates that is personalized for the user based on other user-specific dosage parameters entered by the user for an insulin delivery system (e.g., total daily long-acting insulin dosage (e.g., U/day), a total daily dose of insulin (e.g., total of long and quick acting), a carbohydrate-to-insulin ratio, an insulin sensitivity factor, a glucose setpoint, or a combination thereof). In some cases, the number of carbohydrates assigned to each preset icon or button can be personalized over time based on estimations of the size of each meal consumed when that icon or button is selected based on a glucose response after the consumption of each meal. In some cases, the number of carbohydrates assigned to each preset icon or button can be rounded to the nearest 5 grams of carbohydrates and displayed. In some cases, a number of carbohydrates for each button is not displayed. In some cases, a user may manually enter personalized meal sizes for a number of user-selectable icons or buttons. In some cases, a number of carbohydrates assigned to each user-selectable icon or button can be initially set at a predetermined starting point or can be determined based on entered user information, and then iteratively adjusted upward or downward based upon the glycemic response to that selected meal size and bolus over time.

Initial settings for one or more meal announcement buttons 142-144, 221-223, 321-323 included on a device or in a system provided herein can be preset with predetermined values or ranges (e.g., small=20 g or 15-25 g, medium=30 g or 30-45 g, and large=50 g or 50-75 g). Additionally or alternatively, the initial settings can be set based on entered user data or based on one or more user-specific dosage parameters entered into a device or system provided herein. In some cases, initial settings for the one or more user-selectable icons or buttons can be based on an initially entered or determined and programmed total daily long-acting insulin (TDLAI) dose (e.g., U/day). For example, the relationship between the LAI dose [U/day] and Geometric Mean Meal Size [g] as characterized by the line corresponding to the major axis of the hyperellipsoid is: $\mu*MS=12.1*BR0.387$. The relationship between Geometric Mean Meal Size [g] and Geometric Standard Deviation Meal Size is: $\sigma*MS=1.92-\mu*MS/186$ where MS may represent the meal size and BR may represent the basal rate of insulin. Accordingly, initial meal size groups may correspond to predetermined percentiles of the Meal Size distribution by combining the above equations, optionally rounding meal size groups to the nearest 1.5, or 10 grams. In some cases, the relationship between typical meal sizes and other user-specific dosage parameters can be determined according to population statistics. In some cases, the number of carbohydrates associated with each user-selectable icon or button can be displayed on and/or adjacent to the user-selectable icon or button, which can help a user understand how to use the insulin delivery device or system to avoid deskilling the user. For example, seeing the number of carbohydrates assumed for each meal size helps a user that thinks about meals in terms of carbohydrates to adjust to using buttons to indicate a size of a meal. Additionally, by starting with display numbers rounded to the nearest 5 grams, the user can perceive that precision is not required, thus also reducing the cognitive burden on the user. Additionally, as the system iterates to personalize the amount of carbohydrates for each particular user-selectable icon or button, the system can adjust these numbers by smaller units (e.g., by 1 gram) to demonstrate to the user that the system is adjusting the number of carbohydrates associated with user-selectable icon or button.

In some cases, the user interface may be configured such that a PWD may interact with the user interface to enter more detailed information regarding the bolus size outside of the default options. For example, a PWD may be presented with a series of pre-set sizes that are readily adjustable in increments of 5 g by selecting a size and scrolling up or down. By interacting further with the user device (e.g., pressing and holding on the meal size), the user may have the option to manually input a bolus size or adjust the size in increments of 1 g.

Methods, systems, and devices provided herein can update the number of carbohydrates associated with each user-selectable icon or button using any suitable method. In some cases, methods, systems, and devices can use postprandial blood glucose data (e.g., between 1 hour and 3 hours after an announced meal) to evaluate whether the PWD likely consumed significantly more or significantly less carbohydrates than programmed for the user-selectable icon or button. In some cases, one or more postprandial blood glucose thresholds can be used to evaluate the match between the amount of carbohydrates consumed and the amount of carbohydrates associated with a selected user-selectable meal icon or button. For example, methods, devices, and systems provided herein can ask a user for a postprandial blood glucose reading from a glucose sensor, glucose monitor, or blood glucose meter. In some cases, a glucose sensor can be a flash glucose monitor and methods, systems, and devices provided herein can prompt the user to interrogate the flash glucose monitor at a predetermined postprandial time period. As used herein, the term "flash glucose monitor" may refer to a device configured to provide blood glucose readings in response to a manual invocation of the device, typically by a physical signal (e.g., a button, tap, etc.) or a wireless signal (e.g., a near-field communication (NFC), BLUETOOTH® communication, etc.). Such blood glucose readings may be performed periodically and reported when the device is invoked, or may be taken when invoked. In some cases, methods, devices, and systems provided here can receive postprandial blood glucose data from a continuous glucose monitor. In some cases, methods, systems, and devices provided herein can use a single postprandial blood glucose data point and compare that to one or more upper thresholds and one or more lower thresholds for that period of time to determine whether the number of carbohydrates associated with that user-selectable meal icon or button should be adjusted upward or downward. For example, if a user selects a typical meal icon indicating a meal of 30 grams of carbohydrates, but the 2-hour postprandial blood glucose reading is above 200 mg/dL, the number of grams associated with that icon or button might be adjusted upward by 2 grams, if it is above 170 mg/dL, it might be adjusted upward by 1 gram, if it is below 130 mg/dL, it might be reduced by 1 gram, and if it is below 100 mg/dL, it might be reduced by 2 grams. Accordingly, over time the meal icons would be adjusted to more closely resemble the user's typical consumption patterns in a way that matches the user's mental model surrounding the meals that they eat. The particular thresholds can be determined based on the postprandial time, the number of grams associated with the meal icon or button, the CR, ISF, and daily dose of LAI, and setpoint of the PWD, etc.

In some cases, meal announcement buttons can be personalized based on the time of the day. For example, in some cases, a user may have a larger average dinner and smaller average morning meals, and methods, devices, and systems provided herein can estimate an amount of carbohydrates for a user based on the time of day. In some cases, the amount of carbohydrates and the meal sizes (S, M, L) can be displayed together to help a user understand that the personalization is specific to the user's daily pattern. In some cases, buttons can be personalized based on the day of the week (e.g., a user's weekend meal patterns might be significantly different than during weekdays).

Because diabetes is a highly personal disease that presents the PWD or their caregiver(s) with significant cognitive burdens surrounding the determination of appropriate dosages of insulin, some PWDs or caregivers develop their own techniques (or mental model) for estimating an appropriate dosage of insulin. Although methods, systems, and devices provided herein can be adapted to provide recommendations to a user, the user may be free to dose insulin according to the user's preferences and the user's specific knowledge of what the PWD is about to eat and/or is experiencing (e.g., exercise, sickness, etc.). In some cases, meal announcement buttons can change based on repeated patterns of a user administering doses of insulin above or below a recommended dosage of insulin so that the meal announcement buttons begin to match the user's mental model regarding a typical meal size. Adjustments to an amount of carbohydrates represented by each meal announcement button based on the actual dosage, however, may be determined based on the postprandial blood glucose readings of a PWD. For example, if the postprandial blood glucose readings indicate an appropriate dosage, it can indicate that the user's mental model is appropriate for that meal, and that the system can thus adjust the meal announcement buttons to match the user's mental model (e.g., reduce the size of the meal assumed for a (S) meal based on a repeated pattern of the user administering less insulin than recommended for an (S) meal selection if postprandial blood glucose readings are usually within a predetermined range). However, in some cases, methods, devices, and systems, provided herein can use postprandial blood glucose readings to determine if the user's mental model failed to determine the appropriate dose. In some cases, a high or low postprandial blood glucose reading can prevent methods, systems, and devices provided herein from adjusting the meal announcement buttons based on meals where one or more postprandial blood glucose readings indicate a mismatch between the dose and the meal. For example, if a user administers less insulin than recommended for a selected small meal and has one or more high postprandial blood glucose readings, methods, systems, and devices provided herein can ignore that administration for the personalization of the meal announcement buttons. In some cases, methods, systems, and devices provided herein can provide notices to a user if the user is consistently ignoring the recommended dosages in a way that causes the PWD to go high or low after a meal if the usage pattern indicates a mismatch between the user's mental model and the PWD's physiology and food consumption patterns. For example, if the user is consistently administering less insulin than recommended and consistently having high blood glucose readings after a meal, a notice may indicate to the user that the user should consider administering the recommended doses at meal times in order to achieve better glycemic control. Accordingly, in some cases, methods, systems, and devices provided herein can be designed to improve the match between the user's mental model and the PWD's physiology and food consumption patterns.

In some cases, a remote user interface device 110 can permit a user to manually enter a specific number of carbohydrates into a bolus calculator for a recommendation for a specific meal. In some cases, methods, systems, and devices can use repeated patterns of a user requesting the same meal size recommendation to update the size of a meal announcement button or to add another meal announcement button.

Dose Capture Pen Caps

FIG. 1A depicts a system that can include dose capture pen caps 182 and 184, which can transmit data to and/or from a glucose monitor or sensor 150 and/or to/from a remote user interface device 110. The pen caps in FIG. 1A may or may not include a user interface. Pen caps 182 and 184 can use any suitable technology to determine an amount of insulin that has been administered from insulin pens 160 and 170. In some cases, not shown, insulin pens 160 and 170 can include dose capture technology and can communicate wirelessly with the remote user interface device 110 and/or glucose monitor or sensor 150.

FIGS. 2A-3B depict alternative embodiments of pen caps, 200 and 300, which can be used with an insulin pen to assist a PWD or caregiver (the user) with dosing decisions.

Figure 2A:
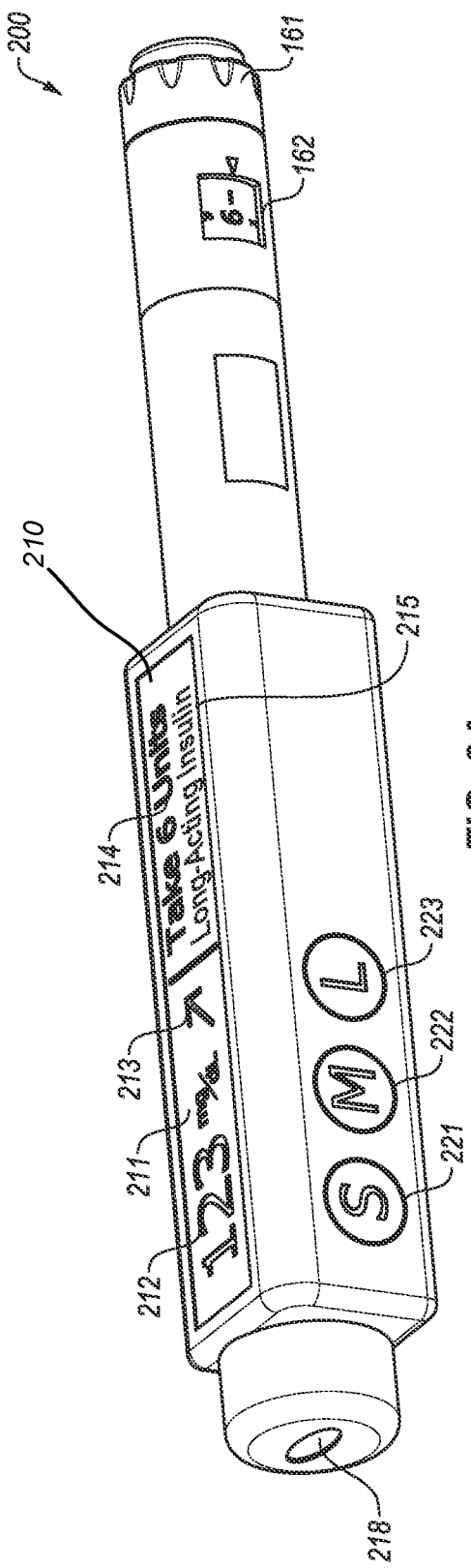
FIGS. 2A and 2B depict an insulin pen with a first exemplary insulin pen cap having some of the features disclosed herein.
Figure 2B:
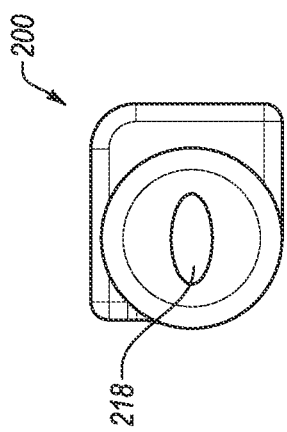

FIGS. 2A and 2B depict an embodiment of a pen cap 200 that includes a display screen 210 that can display an estimated glucose value (EGV) 212, the units for the EGV 211, and a trend indicator for the EGV 213. The display can also provide a recommended dosage 214 and an identification of the type of insulin 215. Pen cap 200 can also include meal announcement buttons 221-223. Additionally, the display may also indicate the time and amount of the previous dosage and/or an IOB value to remind a user about their most recent dosage. Although three meal announcement buttons are shown, in some cases a pen cap can include no meal announcement buttons and meals can be announced on a remote user interface device, such as device 110 as depicted in FIG. 1A. In some cases, pen cap 200 can include a single meal announcement button. In some cases, pen cap 200 can include between 2 and 6 different meal announcement buttons. In some cases, pen cap 200 can include a correction only button. Pen cap 200 can also include one or more indicator lights, such as indicator light 218, which can light up to indicate that it is transferring data, light up to indicate that the user's attention is needed, and/or light up to indicate whether a dose capture functionality is or is not working.

FIGS. 3A and 3B depict another embodiment of a pen cap 300 that includes a touch screen user interface 310 that can include meal announcement buttons 321-323 and display an estimated glucose value (EGV) 312, the units for the EGV 311, a trend indicator for the EGV 313, a recommended dosage 314 and an identification of the type of insulin 315. Additionally, the display may also indicate the time and amount of the previous dosage and/or an IOB value to remind a user about their most recent dosage. Although three meal announcement buttons are shown, the touch screen user interface 310 of pen cap 300 can be customized based on the user's preferences and/or the type of insulin to display different numbers of meal announcement buttons 321-323 and/or to not include meal announcement buttons. For example, if pen cap 300 is placed on a long-acting insulin pen, it may be capable of detecting the type of insulin and automatically updating the display to correctly identify the type of insulin at 315, but also to remove the meal announcement buttons 321-323 and replace them with other content.

Figure 4:
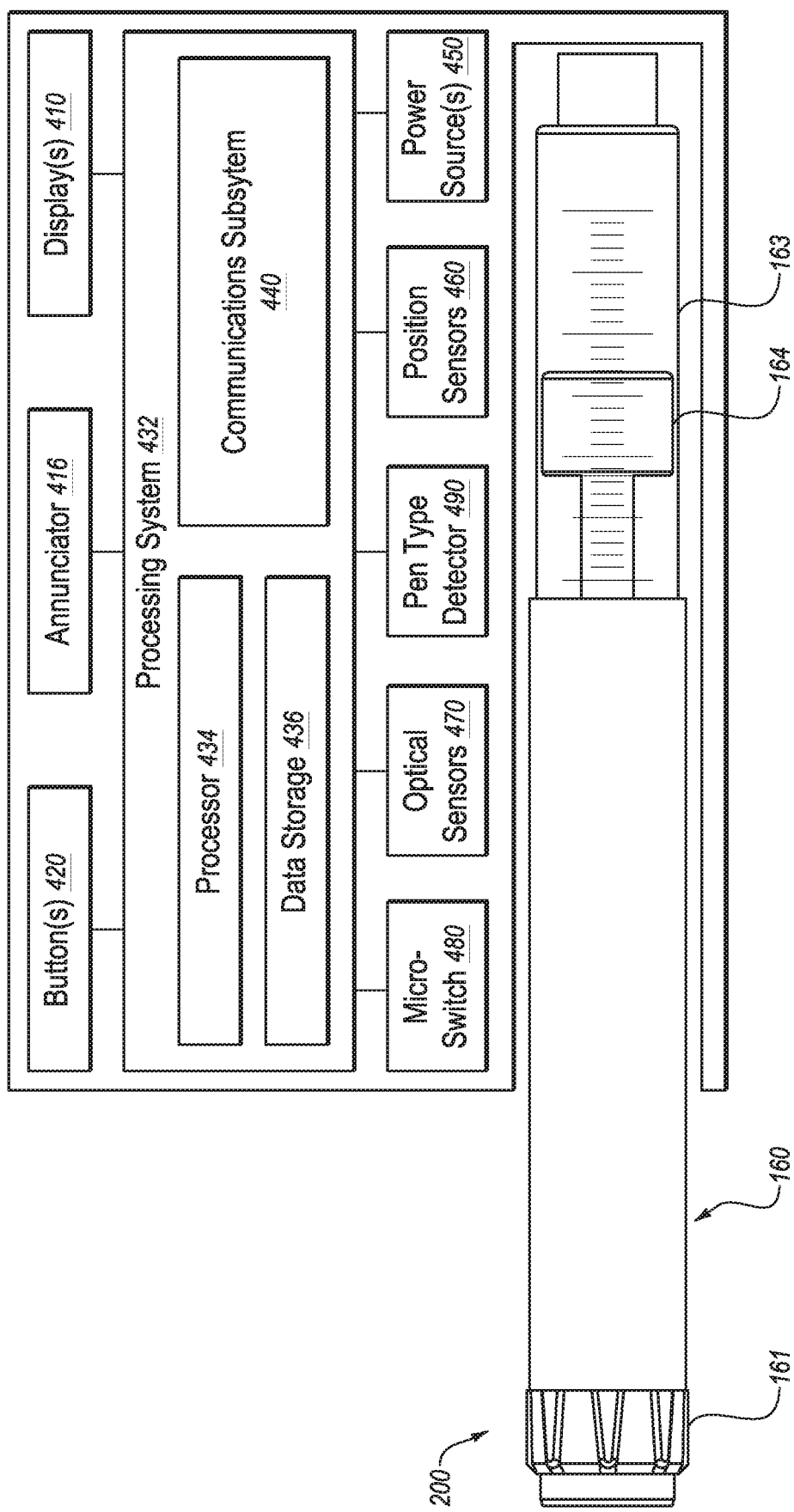
FIG. 4 shows a schematic of internal components that may be included in the insulin pen caps of FIGS. 2A-3B.

Although pen caps 182, 184, 200, and 300 can use any suitable technology to estimate an insulin dosage, FIGS. 4, 5A, and 5B depict exemplary embodiments of pen cap components that may be used to detect a dosage of insulin.

FIG. 4 depicts a representation of the internal components of an exemplary pen cap 400. As shown, the pen cap 400 can include one or more displays 410, one or more buttons 420, and one or more annunciator(s) 416, each controlled by a processing system 432. Processing system 432 includes a processor 434, data storage (or memory) 436, and a communications subsystem 440. The communications subsystem 440 can enable wireless communication between the pen cap and a remote user interface device (e.g., 110 from FIG. 1A) or a glucose sensor or monitor (e.g., 150 from FIG. 1A). In some cases, the communications subsystem 440 can include a near field communications (NFC) chip. In some cases, the communications subsystem 440 can include a BLUETOOTH® Low Energy (BLE) chip. In some cases, the communications subsystem 440 can include an optical communication device, an infrared communication device, a wireless communication device (such as an antenna), and/or chipset (such as a BLUETOOTH® device (e.g., BLUETOOTH® Low Energy, Classic BLUETOOTH®, etc.), a Near-field communication (NFC) device, an 802.6 device (e.g., Metropolitan Area Network (MAN), a ZIGBEE® device, etc.), a WiFi device, a WIMAX® device, cellular communication facilities, etc.), and/or the like. In these and other cases, the communications subsystem 440 can exchange data with a network and/or any other device or system described in the present disclosure. The pen cap 400 includes a power source 450, which may be a rechargeable or non-rechargeable battery. The processing system can determine a pen type from data from a pen type detector 490. The processing system can also determine a position of a plunger within an insulin delivery pen using one or more optical or position sensors and/or micro-switches, such as micro-switch 480, optical sensor(s) 470, and position sensor(s) 460. FIGS. 5A and 5B illustrate the arrangement of a position sensor 460, micro-switch 480, and optical sensor 470 within a pen cap 400. The optical sensor 470 can include a light 471 and photoreceptor 472 positioned on opposite sides of an insulin delivery pen so that light passes through the insulin vial 163 and received by the photoreceptor 472 until the plunger 164 of the insulin pen 160 passes by the optical sensor 470. The tip of insulin pen 160 is received by a slider 462 that slides within the pen to trigger a micro-switch 480 having trigger 482 to tell the pen cap to use optical sensor 470 to identify when the plunger 164 passes the optical sensor 470. Data from position sensor 460, which includes spring 464, slider 462, and proximity sensor 466 to determine the distance that the insulin pen in inserted into the pen cap when the plunger passes the optical sensor 470 and thus determine an amount of insulin remaining in insulin vial 163. Data from prior use of the pen cap 400 can then be used to estimate an amount of insulin delivered to the patient. More detail about how this dose capture technique can be used is disclosed in PCT Publication WO 2017/009724 A1, which is hereby incorporated by reference in its entirety.

Exemplary Use of Dose Capture Device/System

Figure 6A:
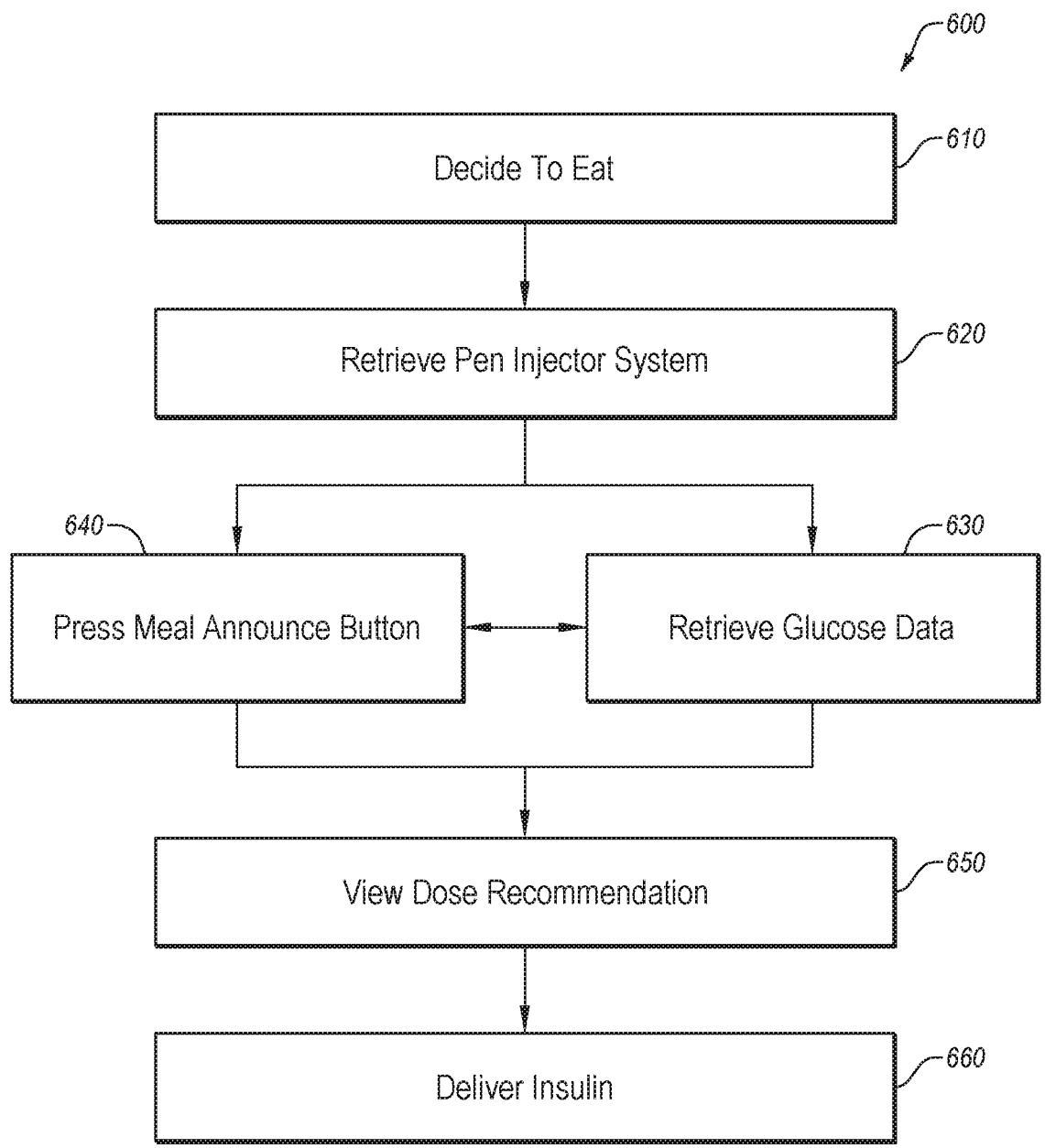
FIG. 6A is a flow chart of how a user may interact with an insulin pen cap provided herein.

FIG. 6A is a flow chart depicting how a user may decide, when eating, to dose insulin using methods, systems, and devices provided herein. As show, process 600 starts with the user deciding to eat something (or deciding to bolus for food already eaten) in step 610, followed by the user retrieving a pen injector in step 620. After retrieving a pen injector, the user may decide to announce a meal in step 640 and/or retrieve glucose data in step 630, which can occur in either order. After announcing a meal and/or retrieving glucose data, the user can view a dosage recommendation, which might appear on a pen cap or may appear on a remote user interface device, in step 650. After viewing the recommendation, the user can then decide how much insulin to deliver and deliver the insulin in step 660.

Figure 6B:
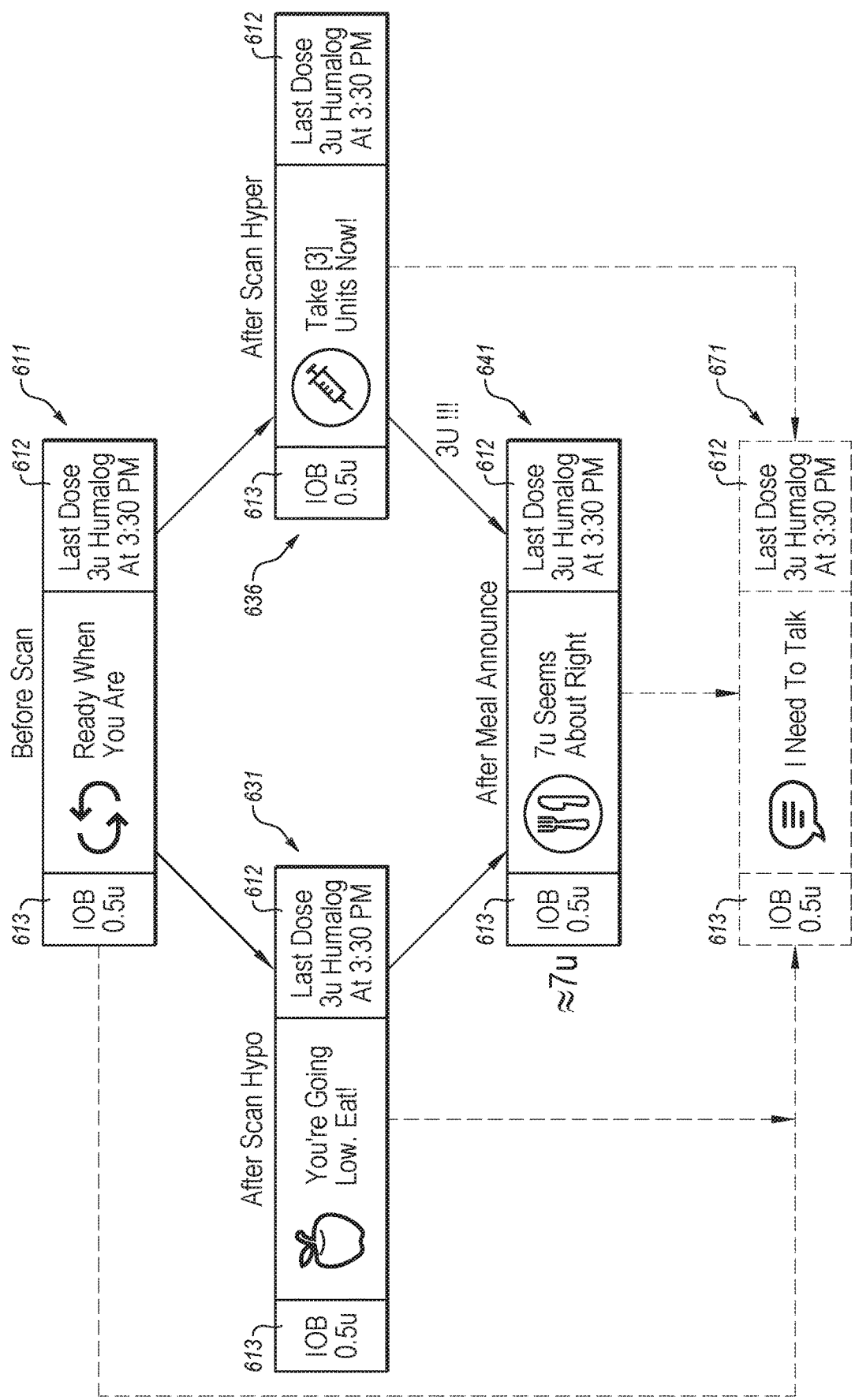
FIG. 6B illustrates exemplary user interfaces that a user may see on a pen cap (or on an insulin delivery pen) during use of certain methods, systems, and devices provided herein.

FIG. 6B depicts an exemplary user interface displays for a pen cap for the user when the user is following process 600. As shown, user screen 611 can indicate that the system is active and display data about a most recent dose 612, such as the type, amount, and time of day, and/or an IOB value 613. If a user obtains a blood glucose value in step 630 that indicates a hypoglycemic condition, user screen 631 can indicate that the user should consume carbohydrates, and may continue to display information about a recent dosage and/or an estimated IOB. If a user obtains a blood glucose value in step 630 that indicates a hyperglycemic condition, user screen 636 can indicate that the user should dose insulin and provide a recommended dosage, and may continue to display information about a recent dosage and/or an estimated IOB. In some cases, the recommended dosage may indicate an amount that a user should add to a dosage that they would otherwise take for a meal. If a user then enters a meal announcement in step 640, user screen 641 can appear and indicate a recommended insulin dosage to account for a meal and the current EGV. User screen 671, however, may appear at any time when the pen cap detects that something has gone wrong or otherwise requires the user's attention. In some cases, pressing buttons on a pen cap can cause the user screen on the pen cap to display more information and/or the user screen 671 can direct the user to troubleshoot issues with the system on a remote user interface device, such as remote user interface device 110 in FIG. 1A.

When a user administers insulin in step 660, the amount of insulin administered may differ from a recommended dosage and/or the recommendation may simply be that the user adjust their mental model of how much to administer for a meal, for example if the user does not make a meal announcement and doses insulin based on user screen 636. As shown in user screen 636, the dosage recommendation may be indicated in brackets to indicate an amount of insulin that should be used to correct for an elevated blood glucose level, and thus the user can add that to the amount of insulin that the user would ordinarily administer for a meal. Accordingly, methods, systems, and devices provided herein can infer the amount of carbohydrates eaten for a meal in the user's mental model based on an amount of insulin delivered by the user. For example, if a user retrieves an EGV from a glucose sensor or monitor in step 630 and sees a recommendation to take 3 units of Humalog in addition to what they would normally take, and then doses 10 units of Humalog, then the methods, systems, and devices provided herein can infer that the user ate a meal and estimate the size of the meal based on the bolus size. The estimated meal size can then be used by the system to further personalize meal announcement buttons (e.g., buttons 142-144, 221-223, and 321-323) and user-specific dosage parameters. Additionally, in some cases a user will announce a meal, but administer an amount of insulin that differs from the amount recommended, in which case methods, systems, and devices provided herein can either ignore the postprandial data for that administration for personalizing the meal announcement buttons (e.g., buttons 142-144, 221-223, and 321-323), but perhaps use the postprandial data for updating user-specific dosage parameters. For example, if a user is about to eat a meal that is between the user's mental model for a medium sized meal and the user's mental model for a large meal, the user might retrieve an EGV (e.g., in step 630) and look at a screen similar to user screen 636 to find out the amount for the correction dosage, and then announce a meal (e.g., in step 640) as a medium meal to see a screen similar to user screen 641 and then announce a meal again (e.g., conduct step 640 again) as a large meal to see a different recommendation, and then the user might deliver an amount of insulin between the two recommendations. Methods, systems, and devices provided herein can use data from a dose capture technique to estimate an amount of insulin actually delivered and use that insulin delivery data to determine an estimated size of each meal, regardless of whether the user announces the meal or follows the recommendation. Additionally, variations from the recommendations and postprandial glucose data can be used to determine adjustments to a number of carbohydrates represented by each meal announcement button e.g., buttons 142-144, 221-223, and 321-323) so that they match the user's mental model, as discussed above.

In many cases, a user will use their own mental model for administering boluses of insulin for meals and only use the system to determine a correction dose after obtaining an EGV (e.g., in step 630) and viewing a screen similar to user screens 631 or 636, which can in some cases indicate a correction dose only or might display two recommendations, (a) an amount to dose or suggestion to eat if they user is only seeking to correct a hyperglycemic or hypoglycemic condition and (b) a change to how much the user would typically dose if the user is eating. In some cases, the calculations can use different equations based on reducing a risk of a hypoglycemic condition. In some cases, a calculation for an amount to change the user's typical dose of insulin if the user is eating can incorporate adjustments based on detected patterns of the user over or under dosing insulin for meals in order to adjust for detected mismatches between the user's mental model and the PWD's physiology and food consumption patterns.

Figure 10A:
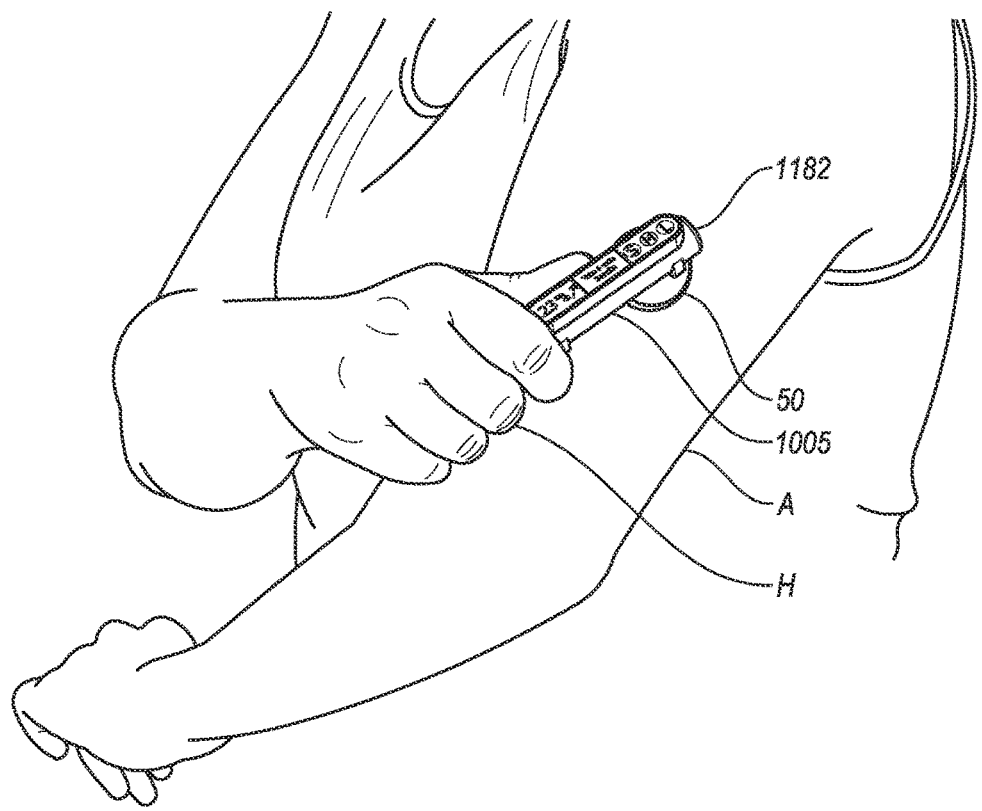
FIGS. 10A and 10B depicts how a user might transmit data between a flash glucose monitor and an insulin pen or insulin pen cap prior to administering insulin.
Figure 10B:
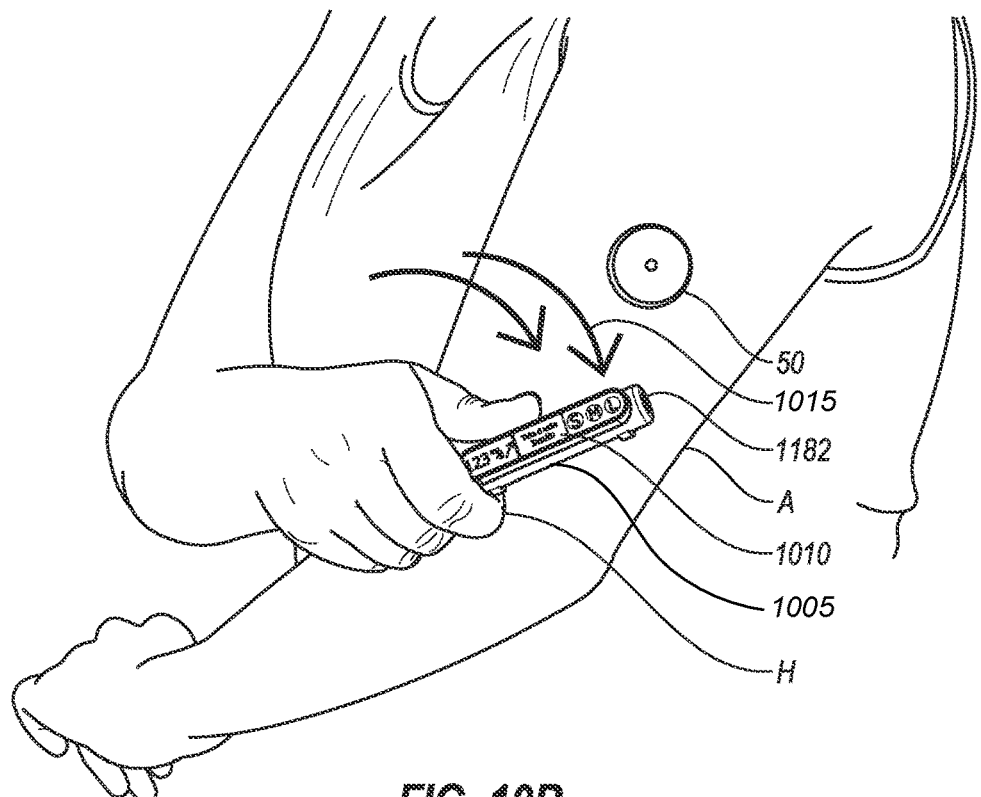

FIGS. 10A and 10B depict exemplary systems for how a user can retrieve blood glucose values from a glucose sensor that can communicate using near field communications by swiping a pen cap 1005 near the glucose sensor 50, optionally with swiping motion 1015. The cap can include a near field communication chip 1182. After swiping, display 1010 can appear on the pen cap 1005.

Wireless Communications and the Pairing Process

Referring back to FIG. 1A, systems provided herein can include one, two, or more pen caps 182 and 184 (or alternatively pen caps 200 and 300 in FIGS. 2A-3B), a remote user interface device 110 (e.g., a smartphone), and a glucose sensor or monitor 150 (e.g., a flash glucose monitor, a continuous glucose monitor, a blood glucose meter), which can all be in wireless communication with each other. In some cases, the glucose sensor or monitor 150 can be a flash glucose monitor adapted to communicate with the pen caps 182 or 184 via near field communication. In some cases, the glucose sensor or monitor 150 can be a continuous glucose monitor adapted to communicate with the pen caps 182 or 184 via radio signals, such as radio signals using BlUETOOTH® Low Energy protocols. Additionally or alternatively, such communication may occur over NFC, WiFi, ZIGBEE®, Classic BLUETOOTH®, or any other communication protocol, device, or technique. In some cases, a flash glucose monitor or a continuous glucose monitor can require a pairing process in order to communicate with other devices and/or can require a warm up period before it is ready to be used. For example, a broadcasting device (which may be either (1) the flash glucose monitor/continuous glucose monitor, glucose sensor or monitor 150 or (2) the pen caps 182 or 184 or other processing device in accordance with the present disclosure) may broadcast a pairing signal that is received by the other device, after which a series of data exchanges or handshakes may occur to establish a secure communication session between the two devices. In some cases, such a pairing procedure may be facilitated by invoking one or more of the buttons of the pen caps 182 or 184. Additionally or alternatively, the pairing procedure may be invoked using a user interface device paired or otherwise coupled with one or both of the glucose sensor or monitor 150 or the pen caps 182 or 184.

Figure 7:
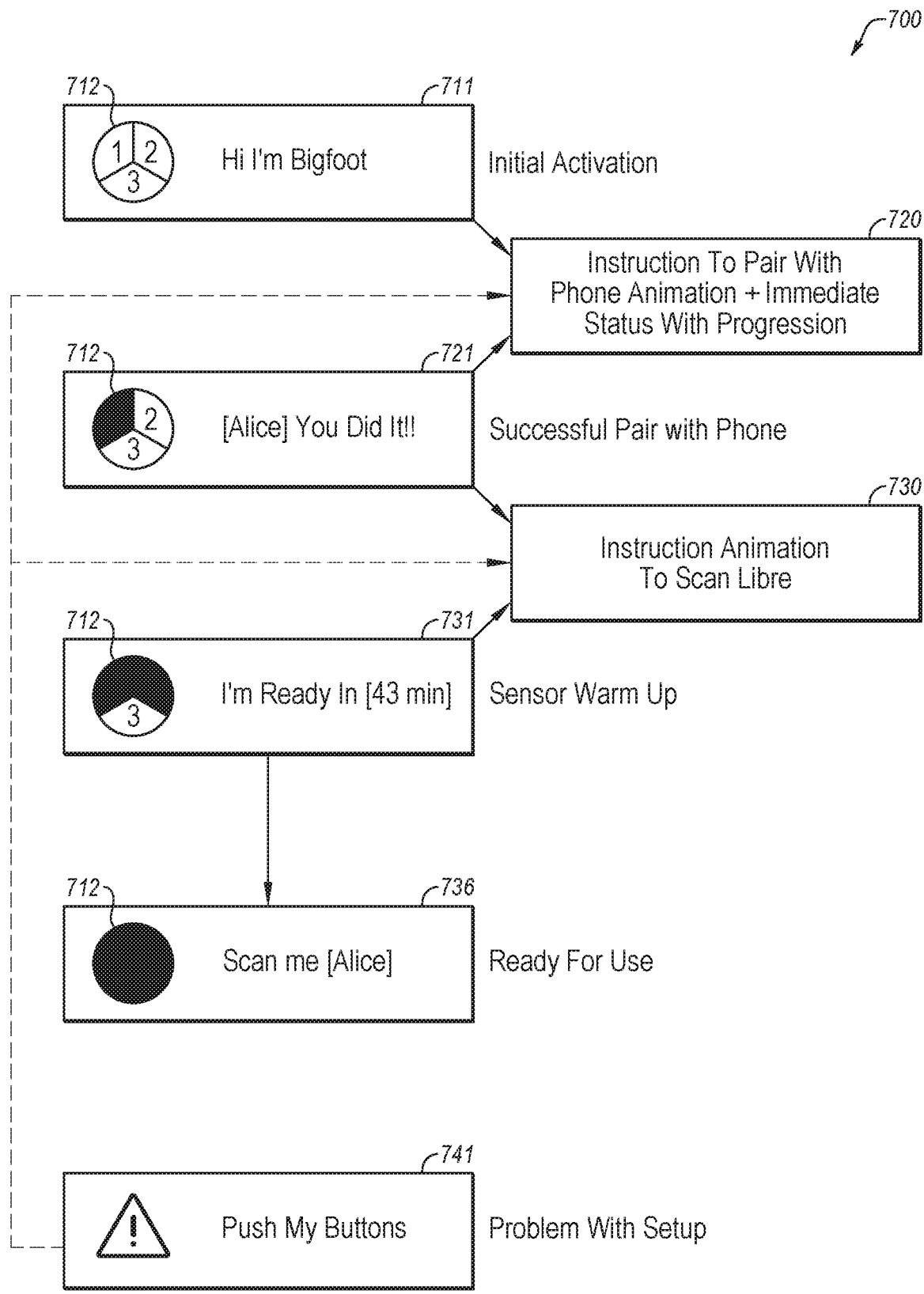
FIG. 7 illustrates exemplary user interfaces that a user may see on a pen cap (or on an insulin delivery pen) when preparing certain methods, systems, and devices provided herein for use.

FIG. 7 illustrates an exemplary process 700 of starting the use of a system, such as the system depicted in FIG. 1A. In user screen 711, a pen cap can include a welcome screen including a connection indicator 712 that indicates that it has not been paired. Connection indicator 712 can include segments that indicate steps that must be completed before the system can be used. In some cases, a screen can be on a remote user interface device (e.g., remote user interface device 110 from FIG. 1A) indicating how the user should pair the pen cap to the remote user interface device. In step 720, the user can receive instructions to pair a remote user interface device (e.g., a smartphone) with the pen cap on the remote user interface device or the pen cap. After the successful pairing of the remote user interface device with the pen cap, screen 721 can appear to indicate the successful pairing with a remote user interface device. Subsequently, in step 730, instructions for connecting the pen cap and/or the remote user interface to a glucose sensor or monitor 150 can appear on the pen cap or the remote user interface. In some cases, the glucose sensor or monitor 150 can be a flash glucose monitor using near field communications, and methods devices, and systems provided here can instruct the user to create a near field communication link between the glucose sensor or monitor 150 and the remote user interface device and/or with the pen cap 182 or 184 to establish a communication link. In screen 731, the pen cap user screen can indicate that a sensor or monitor is warming up, possibly with a countdown clock. In screen 736, the pen cap user screen can indicate that the glucose sensor or monitor 150 is ready for use (after the warm up period has completed). Screen 741 can also appear at any time during the use of the system or during the pairing process to indicate that the pairing has failed, and then return the user to step 720 or 730 to fix the pairing issue. For example, glucose sensors and monitors can have a use life (e.g., 3 days, 7 days, 10 days, 14 days) and require replacement after the use life, so screen 741 may appear after the glucose sensor or monitor has expired, and the user can view instruction for replacing the sensor or monitor and connecting the system to that new glucose sensor or monitor in a step 730. Also, if there is a problem in communicating to a remote user interface device, a screen 741 can appear and bring the user back to step 720 to connect a new remote user interface device or to reconnect the remote user interface device.

Passive and Active Information Gathering

Methods, devices, and systems provided herein can be adapted to gather information about insulin usage and user eating patterns passively without requiring the user to perform extra steps, but be available to help a user determine appropriate actions when called upon by the user. As such, methods, systems, and devices provided here can use dose capture technology in or attached to insulin pens to estimate amounts of insulin delivered to the person with diabetes (PWD). Additionally, estimated blood glucose values (EGVs) can be pushed or pulled to the pen caps and/or to the remote user interface device though wireless communications as discussed above, and be available to the user to help the user make insulin delivery decisions. In some cases, the glucose sensor or monitor 150 can be a flash glucose monitor that requires user interaction to retrieve an EGV. In some cases, a system including a flash glucose monitor can receive both a current EGV and past EGVs from an interrogation of the flash glucose monitor, which can be used by methods, devices, and systems provided herein to make therapy recommendations and to update user-specific dosage parameters.

Figure 8A:
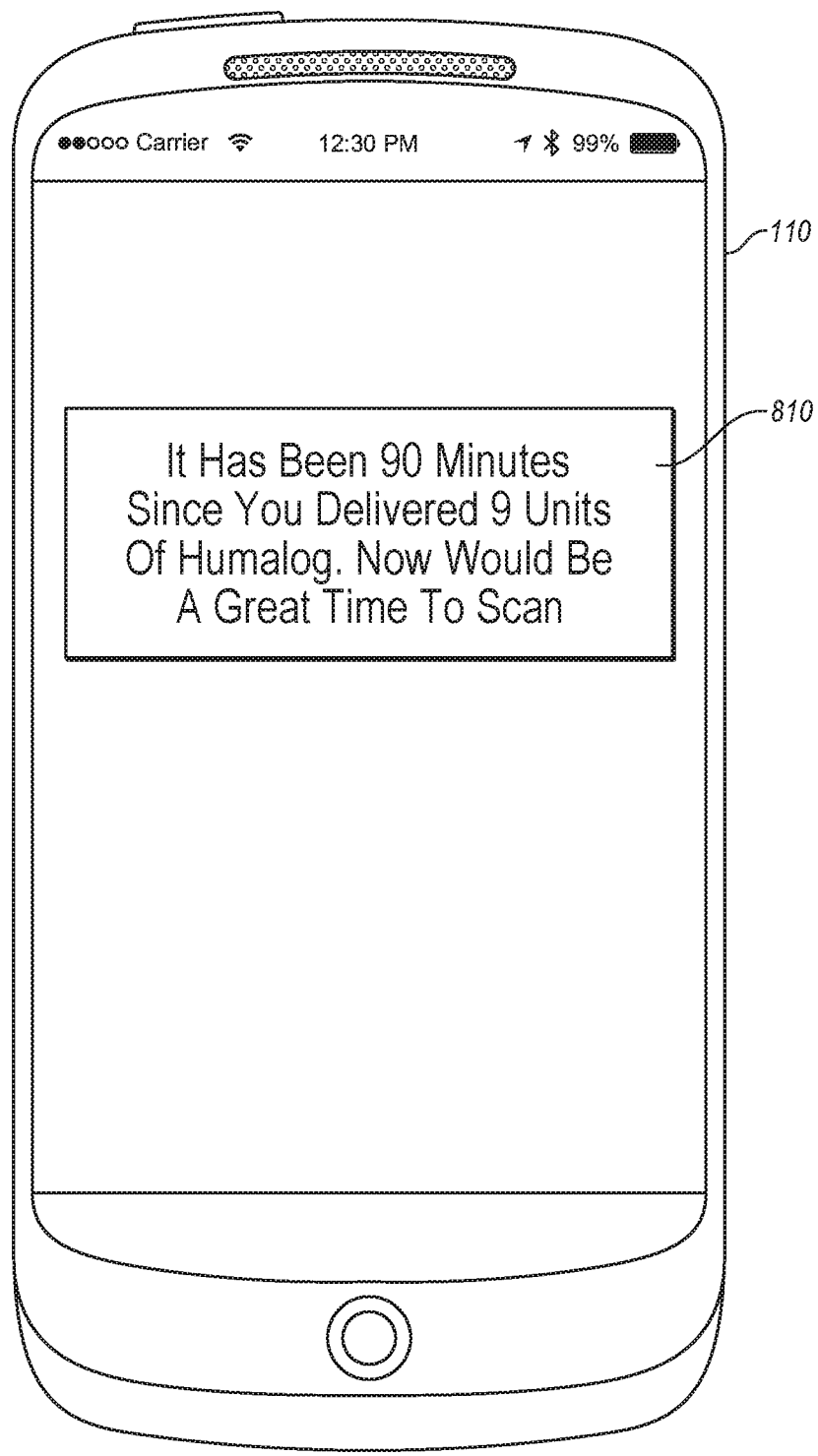
FIGS. 8A and 8B depict notices that may appear on a remote user interface device in some embodiments of methods, systems, and devices provided herein.

In some cases, methods, devices, and systems can include user prompts to request information from the user or to request that the user obtain an EGV, based on risks to the user and/or to obtain data. For example, as discussed above, postprandial data can be used to update the meal announcement buttons. Additionally, postprandial data can be used to update other user-specific dosage parameters. Moreover, after a meal, a user is at an elevated risk of having a hyperglycemic or hypoglycemic condition. Accordingly, in some cases, methods, systems, and devices provided herein can request a user obtain an EGV. For example, in FIG. 8A, a remote user interface device 110 can include a notice 810 displayed at 90 minutes after the administration of a bolus dose of insulin in order to encourage a user to scan a flash glucose monitor. Alternatively, notice 810 can ask the user to obtain blood glucose data from any other suitable glucose monitor or sensor (e.g., from a blood glucose meter requiring a finger stick, etc.) Alternatively, notice 810 can appear on a pen cap or a smart insulin pen. By obtaining the postprandial blood glucose data, methods, systems, and devices provided here can (a) determine whether correction doses may be prudent and/or (b) determine how to personalize meal announcement buttons.

Figure 8B:
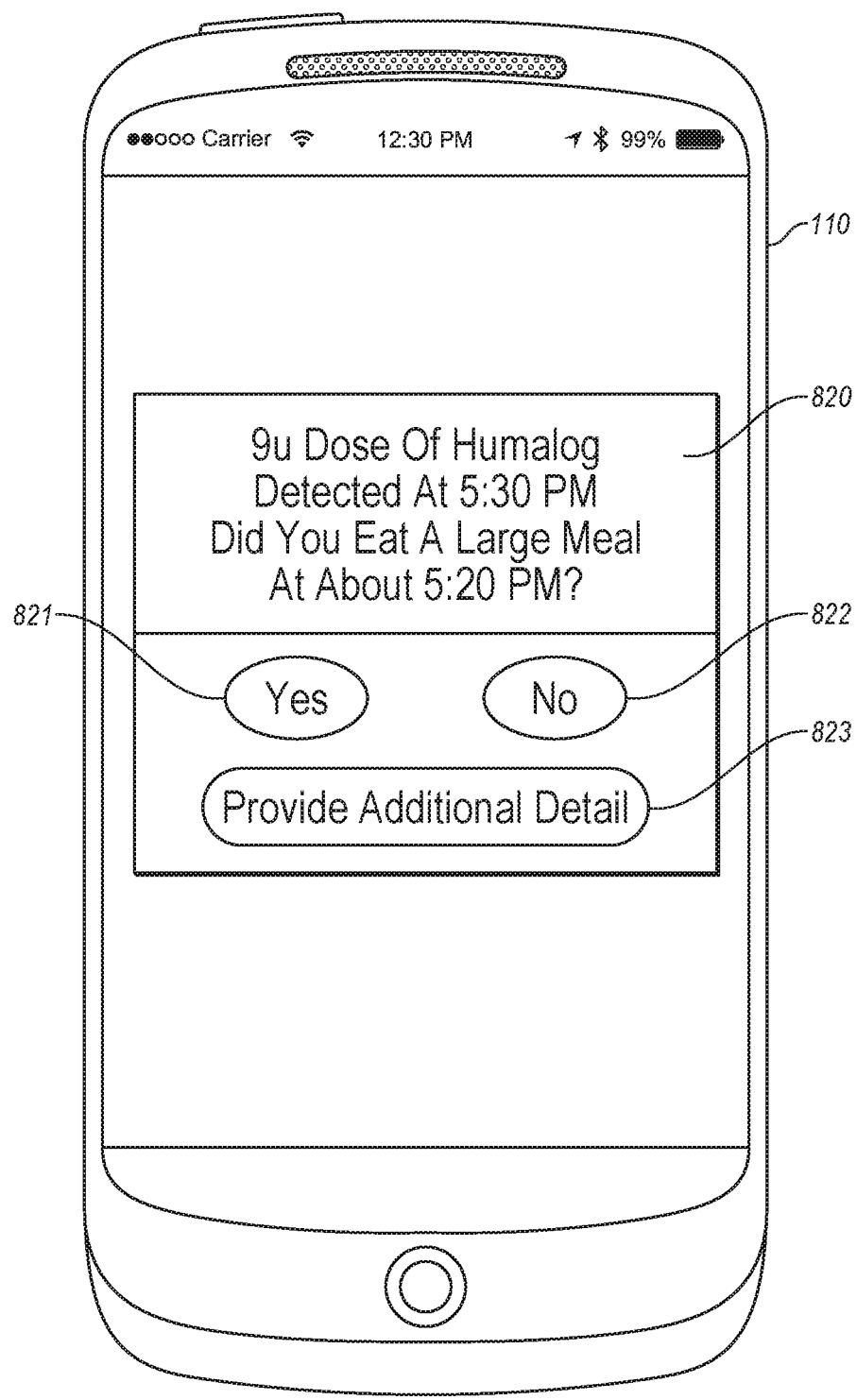

Methods, devices, and systems provided herein can also seek feedback from a user regarding the user's mental model, especially if a user fails to announce a meal size. For example, in some cases, a user determining a dosage of quick-acting insulin may follow the steps shown in FIG. 6B, but stop short of announcing a meal, but instead just bolus for a meal after seeing a suggested correction dose in user screen 636. As discussed above, methods, systems, and devices provided herein can estimate a number of carbohydrates for a meal based on a difference between a recommended correction dosage and an actual dosage. In some cases, methods, devices, and systems provided herein can seek confirmation about an estimated number of carbohydrates from the user when the user accesses a remote user interface. For example, FIG. 8B depicts a message 820 that might appear on a remote user interface device 110 asking the user to confirm by selecting YES 821 or deny by selecting NO 822 whether the PWD ate a particularly sized meal. In some cases, message 820 can appear after blood glucose data is retrieved. In some cases, message 820 can use multiple blood glucose values to determine the likely timing of the meal and the likely size of the meal, which can differ from an amount of carbohydrates inferred based on the insulin size. Additionally or alternatively, methods, systems, and devices of the present disclosure may continue with analysis and/or data collection with an estimated meal size of the PWD even without input from the PWD regarding the size of the meal or even whether or not the PWD consumed a meal. In some cases, a difference between an estimated meal size based on postprandial blood glucose values and insulin delivery data and an estimated meal size based on insulin delivery data alone can indicate a mismatch between the user's mental model and the PWD's physiology and food consumption. In some cases, message 820 can be passive (i.e., without an audible alert), but be available for a user to answer when the user looks at the remote user interface device or opens a mobile app for the system on the remote user interface device. In some cases, message 820 can provide insights showing the user that the methods, systems, and devices understand the user's usage patterns in order to build the user's trust in the devices and systems. In some cases, a user may select button 823 to provide additional details about the bolus. Data received from the user after a meal can then be used to make updates to the meal announcement buttons 142-144, 221-223, 321-323.

Figure 9B:
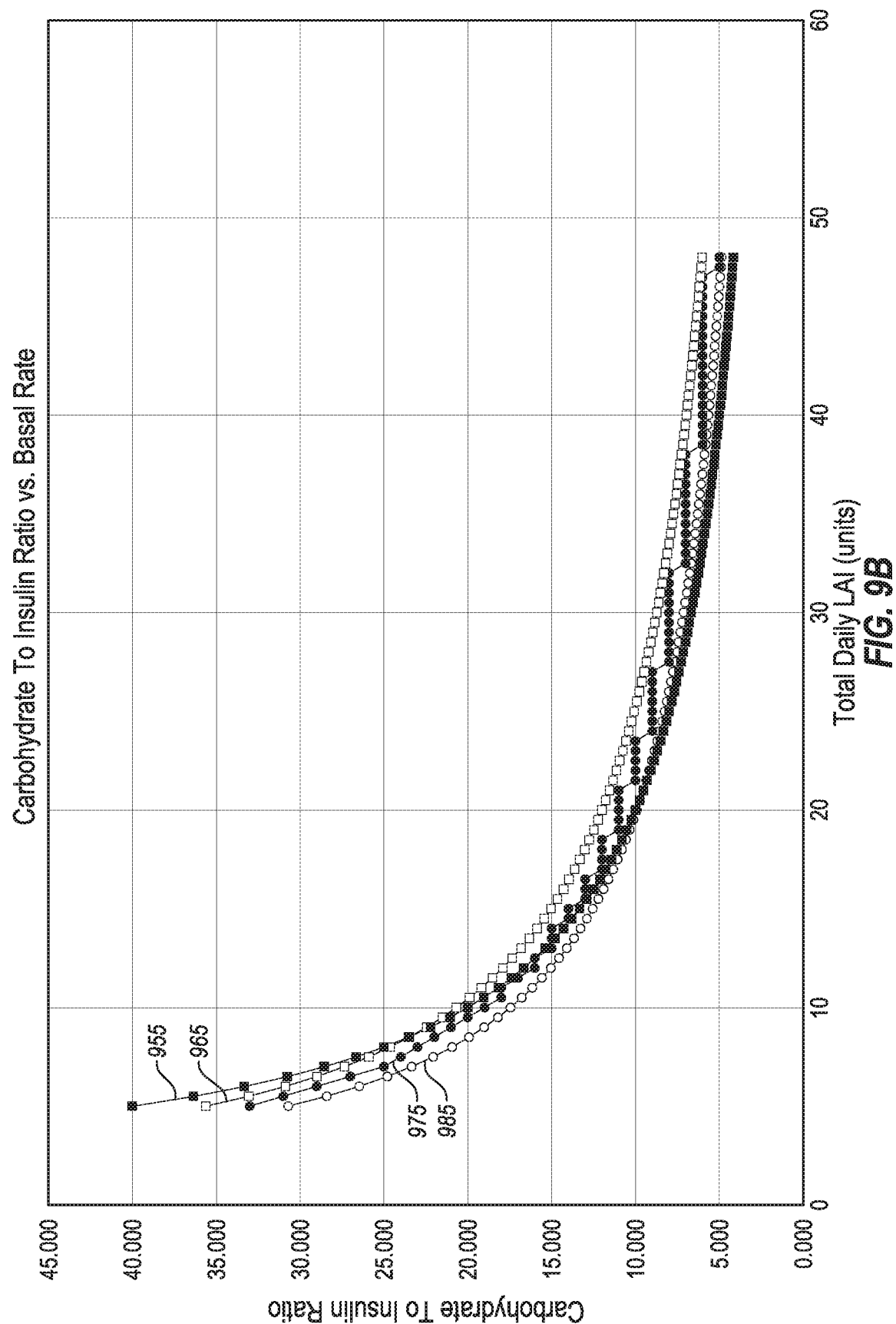

Calculating and Updating Recommendations, User-Specific Dosage Parameters, and Active Insulin Methods, devices, and systems provided herein can use any suitable technique for making recommendations, for updating user-specific dosage parameters (e.g., the person's ISF, CR, Total Daily LAI dosage, etc.), and for estimating amounts of unacted insulin (e.g., for calculating IOB). In some cases, the user-specific dosage parameters can vary depending on the time of day. In some cases, the user-specific dosage parameters can be determined using a fixed relationship between the user-specific dosage parameters. For example, in some cases such as a user having Type 1 Diabetes, a fixed relationship between Total Daily LAI and the PWD's carbohydrate-to-insulin ratio and the PWD's Insulin Sensitivity Factor can be based on fixed mathematical relationships. In some cases, the relationships may be determined by one of the plotted lines 915, 925, 935, 945, 955, 965, 975, or 985 shown in FIGS. 9A and 9B, or any plotted line between lines 915 and 945 and between lines 955 and 985. By having a fixed mathematical relationship between Total Daily LAI and ISF and CR, methods, systems, and devices provided herein can update CR and ISF as a PWD's response to insulin changes over time.

Methods, systems, and devices, can, in some cases, make recommendations to the user to adjust dosages of LAI based on fasting blood glucose readings (e.g., blood glucose readings taken in the morning before the PWD has eaten). In some cases, methods, devices, and systems provided herein can increase by a set number of units (e.g., 0.5 units) based on fasting blood glucose readings being above a threshold and decrease the recommended dosage of LAI based on fasting blood glucose readings being below a different lower threshold. In some cases, methods, devices, and systems can provide recommendations regarding a dosage of LAI and quick-acting insulin (QAI) for if the user fails to deliver the LAI at an appropriate time.

Methods, devices, and systems provided herein can calculate a recommended correction bolus by subtracting a target blood glucose value from the EGV and dividing that number by the Insulin Sensitivity Factor (ISF) and then subtracting the IOB. Methods, devices, and systems provided herein can also calculate a recommended bolus for food consumption by dividing a number of carbohydrates associated with a food announcement button by a carbohydrate-to-insulin ratio (CR) stored for the PWD. Conversely, if a PWD delivers a bolus of insulin after calculating a correction bolus without entering a meal and that bolus differs from the recommended correction bolus, methods, systems, and devices provided herein can calculate an amount of inferred carbohydrates for the meal by subtracting the recommended correction bolus from the amount of insulin delivered and multiplying that number by a CR stored for the user. In other words, Inferred Carbs=(Bolus of Insulin delivered−Recommended Correction Bolus)*CR. Methods, systems, and devices provided herein can then use the calculated inferred carbs in calculating predicted blood glucose levels, which may be used to issue alarms or alerts (e.g., predictive hypoglycemic or predictive hyperglycemic alarms or alerts) to the PWD. In some cases, a Recommended Correction Bolus may be negative. In some cases, devices, systems, and methods provided herein can calculate an amount of inferred carbs by multiplying the bolus by the CR when the user does not input or retrieve an EGV and/or does not have the system calculate a recommended correction bolus. By having methods, systems, and devices infer a number of carbohydrates, methods, devices, and systems provided herein can match the user's mental model without requiring the user to enter data.

Systems for the Treatment of Type 2 Diabetes

In some cases, methods, systems, and devices provided herein can be used to treat a person with type 2 diabetes (PWT2D) and to personalize insulin therapy for the treatment of Type 2 Diabetes (T2D). For example, the system shown in FIG. 1A can be used for the treatment of a PWT2D.

Type 2 Diabetes is often treated by slowly adding treatments. Initially, a PWT2D may be advised to control their diet and to exercise in order to prevent high blood glucose levels, which could be reviewed by logging blood glucose readings taken with a BGM. If diet and exercise is insufficient to achieve glycemic control, which may be defined by an HBA1C value of less than 7% and fasting/pre-meal blood glucose readings of less than 110 mg/dL (but may be personalized based on a number of factors), then the PWT2D may begin treatment of various drugs like GLP-1 RA or SGLT-2i or DPP-4i, which are designed to lower blood glucose levels. If those drugs do not achieve appropriate glycemic control, then the PWT2D may start insulin therapy using one or two injections of LAI, which or without the use of other drugs. Systems, devices, and methods provided herein can be used to assist PWT2Ds with the creating of a data log of blood glucose readings, documenting meals, and reminders of when to take post-meal blood glucose readings even if the PWT2D is not on insulin therapy.

If the PWT2D is taking LAI but not QAI for meals, methods and systems provided herein can be used to make adjustments to the LAI injections in addition to documenting BGM data and meals and issuing reminders. When starting systems and methods provided herein, the user and/or provider of healthcare services may set the initial amounts of LAI based on the PWT2D's previous LAI therapy. If the PWT2D is starting LAI therapy for the first time, the total units of LAI per day may be set at about 0.2 U/kg, or any amount between 0.1 and 0.3 U/kg, when the PWT2D starts the system. For example, if a PWT2D has an A1C of less than 8%, a provider of healthcare may typically set the total LAI therapy at somewhere between 0.1 and 0.2 U/kg. If a PWT2D has an A1C of greater than 8%, a provider of healthcare may typically set the total LAI therapy at somewhere between 0.2 and 0.3 U/kg. For example, a PWT2D weighing 100 kg and having an A1C of 8% might have a provider of healthcare set a total daily dose of LAI at 20 Units (e.g., 10 Units at 8 AM and 10 Units at 8 PM). In some cases, mobile application 10 can include an interface for the PWT2D or their provider of healthcare to enter an initial LAI therapy, which could be updated or adjusted later (both by the algorithm provided below or manually). In some cases, LAI therapy could be initially set and/or updated by a provider of healthcare in a remote web interface that connects to the mobile application through the cloud. In some cases, methods and systems provided herein may require that a qualified healthcare professional enter or confirm the initial LAI therapy.

Methods, devices, and systems provided herein can use and adjust the LAI therapy by tracking blood glucose data and LAI injections. In some cases, the LAI can be upwardly adjusted if an average fasting blood glucose reading for a period of time (e.g., 1 day, 2 days, 3 days, 5 days, 7 days, or more) exceeds a threshold. In some cases, the amount of the adjustment can depend on how much the average fasting blood glucose value exceeds a threshold. For example, in some cases a 3 day average fasting blood glucose value of between 110 and 140 mg/dL would result in an increase of 1 unit LAI per day, a 3 day average fasting blood glucose value of between 140 and 180 mg/dL would result in an increase of LAI by 10%, and a 3 day average fasting blood glucose value of at least 180 mg/dL would result in an increase of LAI by 20%. In some cases, the increase in percentage of LAI can be linearly proportional to the 2 or 3 day average over 110 mg/dL.

In some cases, the LAI can be downwardly adjusted if any blood glucose reading is below a threshold value, which could be hypoglycemia or indicate a risk for hypoglycemia. The decrease can be proportional to the low blood glucose reading. In some cases, if a blood glucose reading is between 40 and 70 mg/dL, the LAI would be decreased by between 10-20%, and a blood glucose reading of less than 40 mg/dL would result in a decrease of between 20-40%. In some cases, methods and systems provided here would decrease LAI 10% for a reading of about 70 mg/dL, decrease it by 20% for a reading of about 40 mg/dL, and decrease it by 40% for a reading of about 30 mg/dL or less.

Typically, if LAI therapy is achieving glycemic control, the system should not produce contradictory upward and downward adjustments. Moreover, glycemic control should result in the absence of hypoglycemia, prevent fasting and pre-meal blood glucose readings of greater than 110 mg/dL, and an A1C of less than 7%. If methods and systems fail to achieve glycemic control after a sufficient period of time (e.g., 1 month, 2 months, etc.), which can be preset or set by a provider of healthcare, the system can send a message to the provider of healthcare to indicate that additional therapy might be considered, which may include drugs like GLP-1 RA or SGLT-2i or DPP-4i or the use of both LAI and QAI therapy. If additional drugs other that QAI are added to the therapy, the system may continue to adjust LAI as described above and determine if glycemic control is achieved after a sufficient period of time (e.g., 1 month, 2 months, etc.).

If a PWT2D switches from LAI therapy alone to therapy using both LAI and QAI, a provider of healthcare can either switch to QAI for only some meals or for all meals. For example, in some cases a provider of healthcare may reduce LAI by 10% or 5 units and set a prandial QAI bolus for the largest meal at that 10% value or the value of 5 units, potentially adding prandial QAI boluses for additional meals if that fails to achieve glycemic control. In some cases, a provider of healthcare may decide to reduce LAI by 50% and set prandial QAI boluses at values to equal the reduction in LAI, perhaps estimating different amounts for different meals. Regardless of the amounts of LAI and prandial QAI boluses and times set by the provider of healthcare, methods and systems provided herein can make adjustments to both LAI and QAI injections based on blood glucose readings. The LAI total units per day could be decreased or increased using the same criteria discussed above for any fasting blood glucose reading. Each prandial QAI bolus can be adjusted by increasing it if a running average blood glucose reading after that meal is above a high threshold and decreasing if a post-meal blood glucose reading is below a low threshold. For example, if a post-meal blood glucose reading 2 hours after a meal is between 70 and 40 mg/dL, the prandial QAI bolus for that meal would be reduced by between 10 and 20%, and it would be reduced by between 20 and 40% if it is below 40 mg/dL. Post-meal blood glucose readings above 140 mg/dL could, for example, result in the system increasing the prandial QAI bolus for that meal by 10% or between 1-2 units of QAI for that meal. Accordingly, the systems and methods presented herein can personalize the size of prandial QAI meal boluses, which may be due to a PWT2D's typical meal size or variations in insulin sensitivity and carbohydrate-to-insulin ratios during the day. Systems provided herein could also issue notices to users if the prandial QAI boluses are producing highly variable post-meal blood glucose readings, indicating to the PWT2D that the meal sizes should remain approximately constant.

Systems, devices, and methods provided herein can also flag unusual circumstances for the user or the provider of healthcare and suggest additional tasks. For example, in some cases, a user may have a post-dinner blood glucose reading of 130 mg/dL, but wake up with a fasting blood glucose reading of greater than 160 mg/dL, which may indicate that the PWT2D may be experience a nighttime low followed by a rebound in blood glucose levels due to a biological response (e.g., the release of glucagon from the liver), thus the system may suggest an occasional additional blood glucose reading at night. A nighttime low may indicate a need to adjust the dinner QAI bolus or the units of LAI. In some cases, methods and systems provided herein may have data regarding a next appointment with a provider of healthcare and ask the PWT2D to take additional blood glucose measurements for a few days leading up to the appointment.

System-Based Inferences

In some cases, methods, devices or systems of the present disclosure may infer certain information by observing and/or analyzing data gathered in accordance with the present disclosure. For example, inferences may be made regarding whether or not a meal was consumed, a size of a meal consumed, whether or not a bolus of insulin was received, and/or a size of a bolus of insulin received.

In some cases, methods, devices or systems of the present disclosure may analyze historic blood glucose readings and note points when blood glucose levels rise, particularly around meal times. By observing rising blood glucose levels, an inference may be made regarding the consumption of a meal. Additionally or alternatively, using user-specific parameters (e.g., carbohydrate-to-insulin ratio (CR), insulin sensitivity factor (ISF), insulin-on-board (IOB), etc.) and/or historic data, a size of a meal may be inferred based on the amount of change in blood glucose levels and data gathered regarding meal sizes for the PWD. For example, if a known amount of insulin is repeatedly given for a PWD as a bolus for a meal and a known response is expected for an expected meal size, variations in that response may convey variations in the size of the meal.

In some cases, methods, devices or systems of the present disclosure may analyze historic blood glucose readings and note points when blood glucose levels decrease. For example, an inference may be made whether or not a user has received a bolus of insulin based on a decrease in blood glucose level based on an expected bolus associated with a meal. For example, an initial increase in blood glucose level around a meal time followed by a decrease in blood glucose level may indicate that a user did, in fact, receive a bolus for a meal. Additionally or alternatively, using user-specific parameters and/or historical data, a size of a bolus may be estimated. For example, if a meal size is known (or estimated) and a typical response is known (or expected) for a PWD, a decrease in blood glucose level may permit methods, devices or systems of the present disclosure to infer a bolus size. In some cases, methods, devices or systems of the present disclosure may use inferences to act as a security check to verify that a PWD received a bolus in association with a meal. For example, a PWD may use an insulin pen for boluses that is not in communication with other components of a system or device of the present disclosure, and such approaches may verify that a bolus was given for a meal.

In some cases, expected variations in blood glucose levels may incorporate the overlap of expected blood glucose levels due to LAI, QAI, and consumed carbohydrates. Such data may be inferred, read from one or more sensors or devices, or input by a user or PWD.

The embodiments described herein may include the use of a special-purpose or general-purpose computer including various computer hardware or software modules, as discussed in greater detail below.

Embodiments described herein may be implemented using computer-readable media for carrying or having computer-executable instructions or data structures stored thereon. Such computer-readable media may be any available media that may be accessed by a general-purpose or special-purpose computer. By way of example, and not limitation, such computer-readable media may include non-transitory computer-readable storage media including Random Access Memory (RAM), Read-Only Memory (ROM), Electrically Erasable Programmable Read-Only Memory (EEPROM), Compact Disc Read-Only Memory (CD-ROM) or other optical disk storage, magnetic disk storage or other magnetic storage devices, flash memory devices (e.g., solid state memory devices), or any other storage medium which may be used to carry or store desired program code in the form of computer-executable instructions or data structures and which may be accessed by a general-purpose or special-purpose computer. Combinations of the above may also be included within the scope of computer-readable media.

Computer-executable instructions comprise, for example, instructions and data which cause a general-purpose computer, special-purpose computer, or special-purpose processing device (e.g., one or more processors) to perform a certain function or group of functions. Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

Any ranges expressed herein (including in the claims) are considered to be given their broadest possible interpretation. For example, unless explicitly mentioned otherwise, ranges are to include their end points (e.g., a range of "between X and Y" would include X and Y). Additionally, ranges described using the terms "approximately" or "about" are to be understood to be given their broadest meaning consistent with the understanding of those skilled in the art. Additionally, the term approximately includes anything within 10%, or 5%, or within manufacturing or typical tolerances.

All examples and conditional language recited herein are intended for pedagogical objects to aid the reader in understanding the disclosure and the concepts contributed by the inventor to furthering the art, and are to be construed as being without limitation to such specifically recited examples and conditions. Although embodiments of the present disclosure have been described in detail, it should be understood that the various changes, substitutions, and alterations could be made hereto without departing from the spirit and scope of the disclosure.

What is claimed is:

1. An insulin delivery system comprising:
an insulin delivery pen;
a glucose monitor or sensor;
a cap for the insulin delivery pen, the cap comprising:
   a memory to store one or more user-specific dosage parameters;
   a user interface comprises a plurality of user-selectable icons, each user-selectable icon representing multiple meal characteristics, each meal characteristic of the multiple meal characteristics of a single user-selectable icon being associated with a time of day; and
a processor in communication with the memory and adapted to receive blood glucose data from the glucose monitor or sensor, the processor being adapted to:
   responsive to the received blood glucose data, present a dosage recommendation with the plurality of user-selectable icons;
   responsive to a selection of a user-selectable icon of the plurality of user-selectable icons, update the presented dosage recommendation to account for the meal characteristics associated with the selected user-selectable icon; and responsive to a determination that a dosage was administered above or below the updated dosage recommendation, adjust the meal characteristic associated with the current time of day of the selected user-selectable icon.

2. The insulin delivery system of claim 1, wherein the glucose monitor or sensor is a flash glucose monitor comprising a flash near field communication circuit, wherein the cap further comprises a system near field communication circuit in communication with the processor, wherein the processor is adapted to receive the blood glucose data via near field communications (NFC) when the system near field communication circuit and the flash near field communication circuit are brought within an NFC communication distance.

3. The insulin delivery system of claim 1, wherein the multiple meal characteristics each initially represent an amount of carbohydrates in 5 gram or 10 gram increments.

4. The insulin delivery system of claim 3, wherein the amount of carbohydrates initially represented by each user-selectable icon of the plurality of user-selectable icons is determined based on an insulin Sensitivity Factor (ISF), a Carb Ratio (CR), a body weight, an age, a total daily basal (TDB) rate, a daily dosage of Long-Acting Insulin, a weight averaged total daily dosage (TDD) of insulin and/or a combination thereof of a person with diabetes (PWD).

5. The insulin delivery system of claim 1, wherein the system is further adapted to update each of the multiple meal characteristics based on postprandial blood glucose data.

6. The insulin delivery system of claim 5, wherein the system comprises a flash glucose monitor comprising a flash near field communication circuit, wherein the system further comprises one or more system near field communication circuits in communication with the processor, wherein the processor is adapted to receive the postprandial blood glucose data via near field communications (NFC) when the one or more system near field communication circuits and the flash near field communication circuit are brought within an NFC communication distance, wherein the processor is adapted to send a prompt to a user to retrieve the postprandial blood glucose data by bringing one of the one or more system near field communication circuits into close proximity to the flash glucose monitor at a predetermined time after insulin is delivered to the user.

7. The insulin delivery system of claim 1, wherein the system is adapted to determine an initial setting for each of the multiple meal characteristics of each user-selectable icon based on a user-entered total daily basal dose.

8. The insulin delivery system of claim 1, wherein the system further comprises a mobile application in wireless communication with the cap.

9. A cap for an insulin delivery pen, the cap comprising:
a memory to store one or more user-specific dosage parameters;
a user interface comprises a plurality of user-selectable icons, each user-selectable icon representing multiple meal characteristics, each meal characteristic of the multiple meal characteristics of a single user-selectable icon being associated with a time of day; and
a processor in communication with the memory and adapted to receive blood glucose data from a glucose monitor or sensor, the processor being adapted to:
responsive to the received blood glucose data, present a dosage recommendation with the plurality of user-selectable icons;
responsive to a selection of a user-selectable icon of the plurality of user-selectable icons, update the presented dosage recommendation to account for the meal characteristics associated with the selected user-selectable icon; and
responsive to a determination that a dosage was administered above or below the updated dosage recommendation, adjust the meal characteristic associated with the current time of day of the selected user-selectable icon.

10. The cap of claim 9, further comprising a flash near field communication circuit for receiving the blood glucose data from the glucose monitor or sensor.

11. The cap of claim 9, wherein the user interface is adapted to display a blood glucose value received from a glucose monitor or sensor.

12. The cap of claim 11, wherein the cap further comprises one or more system near field communication circuits in communication with the processor, wherein the processor is adapted to receive blood glucose data via near field communications (NFC) with the glucose monitor or sensor when the one or more system near field communication circuits is brought within an NFC communication distance of the glucose monitor or sensor.

13. The cap of claim 9, wherein the cap is adapted to determine an initial setting for each of the multiple meal characteristics of each user-selectable icon based on a user-entered total daily basal dose.

14. The cap of claim 9, wherein the cap is in wireless communication with a mobile application.

15. An insulin delivery system comprising:
an insulin delivery pen;
a blood glucose monitor or sensor;
a cap for the insulin delivery pen, the cap comprising:
a user interface comprising a plurality of user-selectable icons or buttons, each user-selectable icon or button representing multiple meal characteristics, each meal characteristic of the multiple meal characteristics of a single user-selectable icon or button being associated with a time of day;
a memory to store one or more user-specific dosage parameters; and
a processor in communication with the memory and adapted to receive blood glucose data from the blood glucose monitor or sensor, the processor being adapted to:
responsive to the received blood glucose data, present with the plurality of user-selectable icons or buttons a dosage recommendation;
responsive to a selection of a user-selectable icon or button of the plurality of user-selectable icons or buttons, update the presented dosage recommendation to account for the meal characteristics associated with the selected user-selectable icon; and
responsive to a determination that a dosage was administered above or below the updated dosage recommendation, adjust the meal characteristic associated with the current time of day of the selected user-selectable icon or button.

16. The insulin delivery system of claim 15, wherein the blood glucose monitor or sensor is a flash glucose monitor comprising a flash near field communication circuit, wherein the cap further comprises a system near field communication circuit in communication with the processor, wherein the processor is adapted to receive the blood glucose data via near field communications (NFC) when the system near field communication circuit and the flash near field communication circuit are brought within an NFC communication distance.

17. The insulin delivery system of claim 15, wherein the processor is adapted to update each of the multiple meal characteristics of each user-selectable icon or button based on the blood glucose data comprising postprandial blood glucose data.

18. The insulin delivery system of claim 15, wherein the processor is adapted to update each of the multiple meal characteristics of each user-selectable icon or button based on the blood glucose data after a user has selected one of the plurality of user-selectable icons or buttons.

19. The insulin delivery system of claim 15, wherein the processor is adapted to determine an initial setting for each of the multiple meal characteristics of each user-selectable icon or button based on a user-entered total daily basal dose.

20. The insulin delivery system of claim 15, wherein the user interface comprises a display of a pen cap for use with an insulin pen.

\* \* \* \* \*